(12) United States Patent
Torgerson

(10) Patent No.: US 11,219,763 B2
(45) Date of Patent: Jan. 11, 2022

(54) HIGH FREQUENCY STIMULATION USING LOW FREQUENCY TITRATION GAUGE

(71) Applicant: Medtronic, Inc., Minneapolis, MN (US)

(72) Inventor: Nathan A. Torgerson, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 223 days.

(21) Appl. No.: 16/345,645

(22) PCT Filed: Oct. 5, 2017

(86) PCT No.: PCT/US2017/055294
§ 371 (c)(1),
(2) Date: Apr. 26, 2019

(87) PCT Pub. No.: WO2018/080754
PCT Pub. Date: May 3, 2018

(65) Prior Publication Data
US 2020/0054879 A1 Feb. 20, 2020

Related U.S. Application Data

(60) Provisional application No. 62/446,051, filed on Jan. 13, 2017, provisional application No. 62/414,440, filed on Oct. 28, 2016.

(51) Int. Cl.
*A61N 1/36* (2006.01)
*A61N 1/05* (2006.01)

(52) U.S. Cl.
CPC ..... *A61N 1/36071* (2013.01); *A61N 1/36132* (2013.01); *A61N 1/36135* (2013.01);
(Continued)

(58) Field of Classification Search
CPC ............ A61N 1/36071; A61N 1/36135; A61N 1/36164; A61N 1/36185; A61N 1/36132;
(Continued)

(56) References Cited

U.S. PATENT DOCUMENTS 5,603,726 A 2/1997 Schulman et al.
5,800,465 A 9/1998 Thompson et al.
(Continued)

FOREIGN PATENT DOCUMENTS

CN 102921105 B 2/2013
CN 107050645 A 8/2017
(Continued)

OTHER PUBLICATIONS

"St. Jude's Prodigy Neurostimulator with Burst Technology," Medgadget, Mar. 20, 2014, 4pp.
(Continued)

*Primary Examiner* — Amanda K Hulbert
*Assistant Examiner* — Natasha Patel
(74) *Attorney, Agent, or Firm* — Shumaker & Sieffert, P.A.

(57) ABSTRACT

The techniques of the disclosure describe example medical devices, systems, and methods for delivering stimulation therapy comprising a first set of a plurality of pulses having a first amplitude, and a second set of a plurality of pulses having a second amplitude greater than the first amplitude. The second amplitude is adjusted to an adjusted second amplitude based on second amplitude being less than or greater than activation threshold. The first amplitude is adjusted based on adjusted second amplitude, and therapy is delivered based at least one the adjusted first amplitude.

37 Claims, 11 Drawing Sheets

(52) U.S. Cl.
CPC ..... *A61N 1/36139* (2013.01); *A61N 1/36164* (2013.01); *A61N 1/36171* (2013.01); *A61N 1/36185* (2013.01); *A61N 1/0551* (2013.01); *A61N 1/36062* (2017.08)

(58) Field of Classification Search
CPC ............ A61N 1/36139; A61N 1/36171; A61N 1/36062; A61N 1/0551
See application file for complete search history.

(56) References Cited

U.S. PATENT DOCUMENTS

| | | | |
|---|---|---|---|
| 6,289,247 B1 | 9/2001 | Faltys et al. | |
| 6,314,325 B1 | 11/2001 | Fitz | |
| 6,421,566 B1 | 7/2002 | Holsheimer | |
| 6,505,078 B1 | 1/2003 | King et al. | |
| 6,675,046 B2 | 1/2004 | Holsheimer | |
| 6,850,802 B2 | 2/2005 | Holsheimer | |
| 6,988,006 B2 | 1/2006 | King et al. | |
| 7,333,858 B2 | 2/2008 | Killian et al. | |
| 7,577,480 B2 | 8/2009 | Zeijlemaker | |
| 7,657,318 B2 | 2/2010 | King et al. | |
| 7,689,289 B2 | 3/2010 | King | |
| 7,742,810 B2 | 6/2010 | Moffitt et al. | |
| 7,792,583 B2 | 9/2010 | Miesel et al. | |
| 8,359,103 B2 | 1/2013 | Alataris et al. | |
| 8,504,150 B2 | 8/2013 | Skelton | |
| 8,620,441 B2 | 12/2013 | Greenberg et al. | |
| 8,694,108 B2 | 4/2014 | Alataris et al. | |
| 8,708,934 B2 | 4/2014 | Skelton et al. | |
| 8,712,533 B2 | 4/2014 | Alataris et al. | |
| 8,712,534 B2 | 4/2014 | Wei | |
| 9,002,460 B2 | 4/2015 | Parker | |
| 9,138,582 B2 | 9/2015 | Doan et al. | |
| 9,155,892 B2 | 10/2015 | Parker et al. | |
| 9,339,655 B2 | 5/2016 | Carbunaru | |
| 9,381,356 B2 | 7/2016 | Parker et al. | |
| 9,386,934 B2 | 7/2016 | Parker et al. | |
| 2003/0204223 A1 | 10/2003 | Leinders et al. | |
| 2004/0267333 A1 | 12/2004 | Kronberg | |
| 2005/0065575 A1 | 3/2005 | Dobak | |
| 2006/0229687 A1* | 10/2006 | Goetz | A61N 1/36071 607/46 |
| 2007/0067004 A1 | 3/2007 | Boveja et al. | |
| 2007/0100388 A1 | 5/2007 | Geber | |
| 2008/0221640 A1 | 9/2008 | Overstreet et al. | |
| 2009/0036945 A1 | 2/2009 | Chancellor et al. | |
| 2009/0204173 A1 | 8/2009 | Fang et al. | |
| 2009/0222053 A1 | 9/2009 | Gaunt et al. | |
| 2011/0054570 A1 | 3/2011 | Lane | |
| 2011/0071589 A1 | 3/2011 | Starkebaum et al. | |
| 2011/0125223 A1 | 5/2011 | Carbunaru et al. | |
| 2011/0282412 A1 | 11/2011 | Glukhovsky et al. | |
| 2012/0130444 A1 | 5/2012 | Wei et al. | |
| 2012/0155188 A1 | 6/2012 | Buettner et al. | |
| 2012/0197336 A1 | 8/2012 | Su | |
| 2012/0197338 A1* | 8/2012 | Su | A61N 1/3615 607/41 |
| 2012/0296389 A1 | 11/2012 | Fang et al. | |
| 2013/0060301 A1 | 3/2013 | Polefko et al. | |
| 2013/0079841 A1 | 3/2013 | Su et al. | |
| 2013/0110194 A1 | 5/2013 | Wei | |
| 2013/0208390 A1 | 8/2013 | Singh et al. | |
| 2013/0268021 A1 | 10/2013 | Moffitt | |
| 2013/0289664 A1 | 10/2013 | Johanek | |
| 2014/0005753 A1 | 1/2014 | Carbunaru | |
| 2014/0025146 A1 | 1/2014 | Alataris et al. | |
| 2014/0031896 A1 | 1/2014 | Alataris et al. | |
| 2014/0031905 A1 | 1/2014 | Irazoqui et al. | |
| 2014/0074189 A1 | 3/2014 | Moffitt et al. | |
| 2014/0142549 A1 | 5/2014 | Su et al. | |
| 2014/0142656 A1 | 5/2014 | Alataris et al. | |
| 2014/0142673 A1 | 5/2014 | Alataris et al. | |
| 2014/0243924 A1 | 8/2014 | Zhu et al. | |
| 2014/0243926 A1 | 8/2014 | Carcieri | |
| 2014/0277267 A1 | 9/2014 | Vansickle et al. | |
| 2014/0277281 A1 | 9/2014 | Grandhe | |
| 2014/0277282 A1 | 9/2014 | Jaax | |
| 2014/0296936 A1 | 10/2014 | Alataris et al. | |
| 2014/0364920 A1 | 12/2014 | Doan et al. | |
| 2014/0371813 A1 | 12/2014 | King et al. | |
| 2014/0378941 A1 | 12/2014 | Su et al. | |
| 2014/0379043 A1 | 12/2014 | Howard | |
| 2015/0012064 A1 | 1/2015 | Chen et al. | |
| 2015/0032181 A1* | 1/2015 | Baynham | A61N 1/3615 607/46 |
| 2015/0127062 A1 | 5/2015 | Holley et al. | |
| 2015/0179177 A1 | 6/2015 | Nagao | |
| 2015/0217117 A1 | 8/2015 | Hershey | |
| 2015/0335893 A1 | 11/2015 | Parker | |
| 2015/0360031 A1 | 12/2015 | Bornzin et al. | |
| 2016/0030741 A1 | 2/2016 | Wei et al. | |
| 2016/0082265 A1 | 3/2016 | Moffitt et al. | |
| 2016/0114166 A1 | 4/2016 | Kaula et al. | |
| 2016/0121124 A1* | 5/2016 | Johanek | A61N 1/37264 607/62 |
| 2016/0136420 A1 | 5/2016 | Brink et al. | |
| 2016/0157769 A1 | 6/2016 | Min et al. | |
| 2016/0175594 A1 | 6/2016 | Min et al. | |
| 2016/0271413 A1 | 9/2016 | Vallejo et al. | |
| 2016/0346546 A1 | 12/2016 | Zhu | |
| 2017/0209695 A1 | 7/2017 | Solomon | |
| 2017/0216587 A1 | 8/2017 | Parker | |
| 2018/0056073 A1 | 3/2018 | Togerson | |
| 2018/0110987 A1 | 4/2018 | Parker | |
| 2018/0369592 A1 | 12/2018 | Johanek | |
| 2018/0369593 A1 | 12/2018 | Johanek | |
| 2019/0105499 A1 | 4/2019 | Torgerson | |
| 2020/0038660 A1 | 2/2020 | Torgerson | |

FOREIGN PATENT DOCUMENTS

| | | | |
|---|---|---|---|
| EP | 0679371 | A1 | 4/1995 |
| EP | 2396072 | B1 | 3/2013 |
| EP | 2756864 | A1 | 7/2014 |
| JP | 2007307188 | A | 11/2007 |
| WO | 2002009808 | A1 | 2/2002 |
| WO | 2010058178 | A1 | 5/2010 |
| WO | 2011156286 | A1 | 12/2011 |
| WO | 2014210065 | A1 | 12/2014 |
| WO | 2015000721 | A1 | 1/2015 |
| WO | 2015143509 | A1 | 10/2015 |
| WO | 2015179177 | A1 | 11/2015 |
| WO | 2015179281 | A1 | 11/2015 |
| WO | 2016090420 | A1 | 6/2016 |
| WO | 2017106503 | A1 | 6/2017 |
| WO | 2010123704 | A2 | 10/2018 |

OTHER PUBLICATIONS

Abejon et al., "Back pain coverage with spinal cord stimulation: A different treatment for each patient," International Neuromodulation Society. Jun. 10, 2015; 567, Abstract Only, 1 pp.

Abeloos, et al., "High density stimulation as an alternative to uncomfortable cervical tonic spinal cord stimulation: case report," International Neuromodulation Society 12th World Congress, Jun. 11-15, 2015, Abstract Only, 1 pp.

Breel, et al., "High Density Stimulation: A novel programming paradigm for the treatment of chronic pain," International Neuromodulation Society (INS) 12th World Congress; Jun. 9, 2015, Abstract Only, 1 pp.

Cuellar MD et al., "Effect of high-frequency alternating current on spinal afferent nociceptive transmission," Neuromodulation: Technology at the Neural Interface; Jul.-Aug. 2013; 16(4): pp. 318-327.

Cui, et al., "Effect of spinal cord stimulation on tactile hypersensitivity in mononeuropathic rats is potentiated by simultaneous GABA(B) and adenosine receptor activation," Neuroscience Letters 247: Apr. 1998; pp. 183-186.

Cui et al., "Spinal cord stimulation attenuates augmented dorsal horn release of excitatory amino acids in mononeuropathy via a GABAergic mechanism," Pain 73, Oct. 1997, pp. 87-95.

(56) References Cited

OTHER PUBLICATIONS

De Ridder, et al., "Burst spinal cord stimulation for limb and back pain," World neurosurgery, Nov. 2013; 80(5):642-649 e641.

De Ridder, et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak, MD, et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res. Feb. 8, 2010; 1313: pp. 53-61.

Grider, et al., "High Frequency (1000 Hz) Stimulation Using Commercially Available Implantable Pulse Generator," North American Neuromodulation Society. Dec. 2013, Abstract Only, 2 pp.

Guan et al., "Spinal cord stimulation-induced analgesia: electrical stimulation of dorsal column and dorsal roots attenuates dorsal horn neuronal excitability in neuropathic rats," Anesthesiology. Dec. 2010; 113(6): pp. 1392-1405.

Guan et al., "Spinal Cord Stimulation: Neurophysiological and Neurochemical Mechanisms of Action" Curr Pain Headache Rep DOI 10,1007s11916-014-0260-4, Mar. 2012, pp. 217-225.

Holsheimer, "Computer modelling of spinal cord stimulation and its contribution to therapeutic efficacy," Spinal Cord Aug. 1998, 36: pp. 531-540.

Hunt SP, Mantyh PW. The molecular dynamics of pain control. Nat Rev Neurosci. Feb. 2001;2(2):83-91.

Kemler, et al., "Spinal cord stimulation in patients with chronic reflex sympathetic dystrophy," N Engl J Med, Aug. 31, 2000; 343(9):618-624.

Kilgore, PhD, et al., "Reversible Nerve Conduction Block Using Kilohertz Frequency Alternating Current," Neuromodulation. Aug. 2013, pp. 242-255.

Kumar, et al., "Spinal cord stimulation versus conventional medical management for neuropathic pain: a multicentre randomised controlled trial in patients with failed back surgery syndrome," Pain Jul. 2007; 132(1-2): 179-188.

Likar et al., "High density spinal cord stimulation: a multi-center experience," Abstracts, International Neuromodulation Society 12th World Congress; Jun. 11-15, 2015, 1 pp.

Sweet et al., "High Frequency vs. Burst Stimulation Patterns for Dorsal Columns Stimulation: The Importance of Charge," American Association of Neurological Surgeons, Abstract, Apr. 4, 2014, 2 pp.

Maeda, et al., "Low frequencies, but not high frequencies of bi-polar spinal cord stimulation reduce cutaneous and muscle hyperalgesia induced by nerve injury," Pain; Feb. 2008; 138(1): pp. 143-152.

North M.D. et al., "Spinal cord stimulation versus repeated lumbosacral spine surgery for chronic pain: a randomized, controlled trial," Neurosurgery, Jan. 2005; 56(1): 98-106; discussion 106-107.

North, et al., "Clinical outcomes of 1 kHz subperception spinal cord stimulation (SCS): Results of a prospective randomized controlled crossover trial," Abstracts, International Neuromodulation Society, Jun. 2015, 1 pp.

Ranck Jr., et al., "Which elements are excited in electrical stimulation of mammalian central nervous system: a review," Brain Res. Nov. 21, 1975; 98(3): pp. 417-440.

Replogle, MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Sato, et al., "Spinal cord stimulation reduces hypersensitivity through activation of opioid receptors in a frequency-dependent manner," Eur J Pain. Apr. 17, 2012 (4): pp. 551-561.

Song, et al., "Efficacy of kilohertz-frequency and conventional spinal cord stimulation in rat models of different pain conditions," Neuromodulation Jan. 2014; 17(3): pp. 226-234.

Schu et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.

Shechter et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.

Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Maeda, et al., "Increased c-fos immunoreactivity in the spinal cord and brain following spinal cord stimulation is frequency-dependent," Brain Res. Mar. 9, 2009; 1259: pp. 40-50.

Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.

Smith, et al., "Successful use of high-frequency spinal cord stimulation following traditional treatment failure," Stereotact Funct Neurosurg. Apr. 2015; 93(3): pp. 190-193.

Wille, MD, et al., "Altering Conventional to High Density Spinal Cord Stimulation: An Energy Dose-Response Relationship in Neuropathic Pain Therapy," Neuromodulation: Technology at the Neural Interface, Aug. 2016, 9 pp.

Maggi, et al., "Effect of urethane anesthesia on the micturition reflex in capsaicin-treated rats." Journal of the Autonomic Nervous System, Jan. 1990, 30(3): 247-251.

Walter, et al., "Inhibiting the hyperreflexic bladder with electrical stimulation in a spinal animal model." Neurourology and Urodynamics, 1993, 12:241-253. Applicant points out in accordance with MPEP 609.04(a) that the 1993 year of publication is sufficiently earlier than the effective U.S. filing date of the present application, and any foreign priority date that the particular month of publication is not in issue.

Hubscher, et al., "Convergence and cross talk in urogenital neural circuitries," J. Neurophysiol 110: 1997-2005, first published Aug. 7, 2013, 9 pp.

Snellings et al., "Effects of stimulation site and stimulation parameters on baldder inhibition by electrical nerve stimulation," BJU International, published Aug. 9, 2011, pp. 136-143.

Woock, et al., "Activation and inhibition of the micturition reflex by penile afferents in the cat," Am J. Physiol Regul Intergre Comp Physiol, published Apr. 23, 2008, pp. R1880-R1889.

Bhadra et al., "High frequency electrical conduction block of the pudendal nerve," Journal of Neural Eng., IOP Publishing LTD, published Jun. 3, 2006, 14 pp.

Boger et al., "Bladder Voiding by Combined High Frequency Electrical Pudendal Nerve Block and Sacral Root Stimulation," Neurourology and Urodynamics, Wiley InterScience, vol. 27, Issue 5, Jul. 2, 2008, 6 pp.

Maeda, et al., "Increased c-fos immunoreactivity in the spinal cord and brain following spinal cord stimulation is frequency-dependent," Brain Res. Jan. 6, 2009; 1259: pp. 40-50.

Ebbini et al., "Monitoring and Guidance of Minimally-Invasive Thermal Therapy Using Diagnostic Ultrasound," 31st Annual International Conference of the IEEE EMBS, Sep. 2-6, 2009, 4 pp.

Sherman, "Patch Based Ultrasound: A New Dimension in Therapeutic Ultrasound," Profiles in Excellence 2010, Rutgers University Biomechanical Sports Podiatrist, Podiatry Management, Jun./Jul. 2010, 2 pp.

Protopappas et al., "An Ultrasound Wearable System for the Monitoring and Acceleration of Fracture Healing in Long Bones," IEEE Transactions on Biomedical Engineering, vol. 52, No. 9, Sep. 2005, 12 pp.

(56) References Cited

OTHER PUBLICATIONS

International Search Report and Written Opinion of International Application No. PCT/US2017/055294, dated Feb. 5, 2018, 8 pp.
Partial Search Report from counterpart European Application No. 20208387.9, dated Apr. 1, 2021, 19 pp.
Prosecution History from U.S. Appl. No. 16/339,785, dated Dec. 31, 2020 through Mar. 31, 2021, 29 pp.
Extended Search Report from counterpart European Application No. 20208387.9, dated Jun. 22, 2021, 17 pp.

* cited by examiner

HIGH FREQUENCY STIMULATION USING LOW FREQUENCY TITRATION GAUGE

This application is a U.S. National Stage filing under 35 U.S.C. 371 of International Application No. PCT/US2017/055294, filed Oct. 5, 2017, which claims the benefit of U.S. Provisional Application No. 62/414,440, which was filed on Oct. 28, 2016 and is entitled, "CONTROLLING ELECTRICAL STIMULATION THERAPY" and claims the benefit of U.S. Provisional Application No. 62/446,051, which was filed on Jan. 13, 2017 and is entitled "HIGH FREQUENCY STIMULATION BASED ON LOW FREQUENCY TITRATION GAUGE," the entire contents of each is incorporated herein by reference.

TECHNICAL FIELD

This disclosure generally relates to electrical stimulation therapy.

BACKGROUND

Medical devices may be external or implanted, and may be used to deliver electrical stimulation therapy to patients to various tissue sites to treat a variety of symptoms or conditions such as chronic pain, tremor, Parkinson's disease, epilepsy, urinary or fecal incontinence, sexual dysfunction, obesity, or gastroparesis. FA medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient.

SUMMARY

In some examples, the disclosure describes example medical devices, systems, and techniques for automatically adjusting electrical stimulation therapy delivered to a patient to eliminate or reduce the occurrence of evoked action potentials in tissues of the patient. For example, a medical device system may be configured to determine that electrical stimulation therapy being delivered to a patient according to a set of stimulation parameter values evokes an action potential in a tissue of a patient, e.g., by sensing the evoked compound action potentials in tissue of the patient via one or more sensors. Based on the determination, the medical device system may be configured to adjust one or more of the stimulation parameters values defining the electrical stimulation therapy delivered to the patient to identify a set of therapy parameters values that do not evoke action potentials in a tissue of the patient when delivered.

In some examples, to adjust the electrical stimulation therapy, the medical device system may deliver a series of electrical pulses in which the amplitude of the respective pulses is increased, e.g., by ramping up the amplitude value of the respective pulses. The initial stimulation pulse may have an amplitude such that the delivered stimulation is below the activation threshold and does not evoke an action potential in the tissue of a patient. While the series of pulses is delivered to the patient, the medical device system may monitor the patient to determine when an action potential is evoked by a stimulation pulse. The medical device system may then reduce the amplitude the stimulation to a value below the amplitude of the stimulation pulse that first evoked an action potential in the tissue of the patient, e.g., by a predetermined percentage or to the value of one or the preceding stimulation pulses in the series of delivery pulses. The medical device may then resume delivery of the electrical stimulation to the patient according to the adjusted amplitude value. In this manner, the medical device system may maintain the delivery of electrical stimulation to a patient that is below the activation threshold of the tissue such that action potentials are not evoked in the tissue (e.g., except for brief occurrences of evoked compound action potentials that may trigger the parameter adjustment), while also delivering therapy at a relatively high intensity.

In some examples, during therapy delivery, the medical device system may adjust the therapy delivered to the patient. There may be various causes for adjusting therapy such as change in patient posture, change in efficacy of therapy, change in lead location, change in electrode impedance, etc. However, because stimulation pulses having amplitudes less than the activation threshold tend not to evoke an action potential, there may be limited feedback available to determine whether an adjustment to the therapy is providing effective therapy without patient intervention. In some cases, due to change in patient posture, change in efficacy of therapy, change in lead location, change in electrode impedance, etc., the medical device system may be delivering stimulation pulses having amplitudes greater than the activation threshold, and an adjustment of therapy may be useful to reduce the amplitude of the therapy to below the activation threshold for patient comfort and/or reduction in power consumption. For instance, delivering stimulation pulses above the activation threshold may not provide any additional therapeutic effect, but utilizes more power than delivering stimulation pulses below the activation threshold.

The medical device system may be configured to deliver stimulation pulses having a first amplitude, and deliver stimulation pulses having a second, greater amplitude, where one or more stimulation pulses having the second amplitude are intermingled with groups of stimulation pulses having the first amplitude. The medical device system may determine whether an action potential is evoked in response to delivery of a pulse having the second amplitude. If an action potential is not evoked, the medical device system may determine that the amplitude of the therapy is too low, and adjust the second amplitude upwards until delivery of a pulse having an adjusted second amplitude evokes an action potential (e.g., until the adjusted second amplitude is greater than or equal to the activation threshold). If an action potential is evoked, the medical device system may determine that the amplitude of the therapy is too high, and adjust the second amplitude downwards until delivery of a pulse having an adjusted second amplitude does not evoke an action potential (e.g., until the adjusted second amplitude is less than or equal to the activation threshold). The medical device system may adjust the first amplitude to an adjusted first amplitude based on the adjusted second amplitude, and deliver stimulation therapy that includes pulses having the adjusted first amplitude and pulses having the adjusted second amplitude.

In one example, this disclosure describes a method comprising: controlling delivery of an electrical stimulation therapy from an implantable medical device to a patient according to at least one therapy program, wherein the electrical stimulation therapy is configured to provide pain relief to the patient without substantially resulting in paresthesia perceived by the patient; and periodically adjusting the electrical stimulation therapy delivered to the patient in response to detected compound action potentials, wherein the adjustment to the electrical stimulation therapy is configured to eliminate action potentials in tissue of the patient evoked by the delivered electrical stimulation, and wherein the controlling and the adjusting are performed via one or more processors.

In another example, this disclosure describes a method comprising: controlling delivery of an electrical stimulation therapy from an implantable medical device to a patient according to at least one therapy program, wherein the electrical stimulation therapy is configured to provide pain relief to the patient without substantially resulting in paresthesia perceived by the patient; and in response to detecting an electrically-evoked compound action potential, adjusting the electrical stimulation therapy delivered to the patient to eliminate action potentials in tissue of the patient evoked by the delivered electrical stimulation, and wherein the controlling and the adjusting are performed via one or more processors In another example, this disclosure describes a method comprising: controlling delivery of an electrical stimulation therapy from an implantable medical device to a patient according to at least one therapy program, wherein the electrical stimulation therapy is configured to provide pain relief to the patient without substantially resulting in paresthesia perceived by the patient; and while detecting an electrically-evoked compound action potential, adjusting at least one parameter of the at least one therapy program defining the electrical stimulation therapy delivered to the patient until the electrically evoked compound action potential is no longer detected, and wherein the controlling and the adjusting are performed via one or more processors.

In another example, this disclosure describes a medical device system comprising: a stimulation generator configured to deliver electrical stimulation to a patient; and a processor configured to control delivery of an electrical stimulation therapy from the stimulation generator to the patient according to at least one therapy program, wherein the electrical stimulation therapy is configured to provide pain relief to the patient without substantially resulting in paresthesia perceived by the patient; and periodically adjust the electrical stimulation therapy delivered to the patient in response to detected compound action potentials, wherein the adjustment to the electrical stimulation therapy is configured to eliminate action potentials in tissue of the patient evoked by the delivered electrical stimulation, and wherein the controlling and the adjusting are performed via one or more processors.

In another example, this disclosure describes a medical device system comprising: a stimulation generator configured to deliver electrical stimulation to a patient; and a processor configured to: control delivery of an electrical stimulation therapy from an implantable medical device to a patient according to at least one therapy program, wherein the electrical stimulation therapy is configured to provide pain relief to the patient without substantially resulting in paresthesia perceived by the patient; and in response to detecting an electrically-evoked compound action potential, adjust the electrical stimulation therapy delivered to the patient to eliminate action potentials in tissue of the patient evoked by the delivered electrical stimulation.

In another example, this disclosure describes a medical device system comprising: a stimulation generator configured to deliver electrical stimulation to a patient; and a processor configured to: control delivery of an electrical stimulation therapy from an implantable medical device to a patient according to at least one therapy program, wherein the electrical stimulation therapy is configured to provide pain relief to the patient without substantially resulting in paresthesia perceived by the patient; and while detecting an electrically-evoked compound action potential, adjust at least one parameter of the at least one therapy program defining the electrical stimulation therapy delivered to the patient until the electrically evoked compound action potential is no longer detected.

In another example, this disclosure describes a medical device system comprising: means for controlling delivery of an electrical stimulation therapy from an implantable medical device to a patient according to at least one therapy program, wherein the electrical stimulation therapy is configured to provide pain relief to the patient without substantially resulting in paresthesia perceived by the patient; and means for periodically adjusting the electrical stimulation therapy delivered to the patient in response to detecting compound action potentials, wherein the adjustment to the electrical stimulation therapy is configured to eliminate action potentials in tissue of the patient evoked by the delivered electrical stimulation, and wherein the controlling and the adjusting are performed via one or more processors.

In another example, the disclosure describes a method comprising delivering stimulation therapy comprising a first set of a plurality of pulses having a first amplitude, and a second set of a plurality of pulses having a second amplitude greater than the first amplitude, wherein one or more pulses of the second set of plurality of pulses are intermingled with sequential groups of pulses of the first set of plurality of pulses, adjusting the second amplitude to an adjusted second amplitude until the adjusted second amplitude is one of greater than or equal to an activation threshold based on the second amplitude being less than the activation threshold, or less than or equal to the activation threshold based on the second amplitude being greater than the activation threshold, adjusting the first amplitude to an adjusted first amplitude based on the adjusted second amplitude, and delivering stimulation therapy based at least on the adjusted first amplitude.

In another example, the disclosure describes a medical system comprising at least one stimulation generator, and a processing circuitry comprising at least one of fixed-function or programmable circuitry. The processing circuitry is configured to cause the at least one stimulation generator to deliver stimulation therapy comprising a first set of a plurality of pulses having a first amplitude, and a second set of a plurality of pulses having a second amplitude greater than the first amplitude, wherein one or more pulses of the second set of plurality of pulses are intermingled with sequential groups of pulses of the first set of plurality of pulses, adjust the second amplitude to an adjusted second amplitude until the adjusted second amplitude is one of greater than or equal to an activation threshold based on the second amplitude being less than the activation threshold, or less than or equal to the activation threshold based on the second amplitude being greater than the activation threshold, adjust the first amplitude to an adjusted first amplitude based on the adjusted second amplitude, and cause the at least one stimulation generator to deliver stimulation therapy based at least on the adjusted first amplitude.

In another example, the disclosure describes a medical system comprising means for delivering stimulation therapy comprising a first set of a plurality of pulses having a first amplitude, and a second set of a plurality of pulses having a second amplitude greater than the first amplitude, wherein one or more pulses of the second set of plurality of pulses are intermingled with sequential groups of pulses of the first set of plurality of pulses, means for adjusting the second amplitude to an adjusted second amplitude until the adjusted second amplitude is one of greater than or equal to an activation threshold based on the second amplitude being less than the activation threshold, or less than or equal to the activation threshold based on the second amplitude being greater than the activation threshold, means for adjusting the first amplitude to an adjusted first amplitude based on the adjusted second amplitude, and means for delivering stimulation therapy based at least on the adjusted first amplitude.

In another example, the disclosure describes a computer-readable storage medium storing instructions that when executed cause one or more processors to cause at least one stimulation generator to deliver stimulation therapy comprising a first set of a plurality of pulses having a first amplitude, and a second set of a plurality of pulses having a second amplitude greater than the first amplitude, wherein one or more pulses of the second set of plurality of pulses are intermingled with sequential groups of pulses of the first set of plurality of pulses, adjust the second amplitude to an adjusted second amplitude until the adjusted second amplitude is one of greater than or equal to an activation threshold based on the second amplitude being less than the activation threshold, or less than or equal to the activation threshold based on the second amplitude being greater than the activation threshold, adjust the first amplitude to an adjusted first amplitude based on the adjusted second amplitude, and cause the at least one stimulation generator to deliver stimulation therapy based at least on the adjusted first amplitude.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
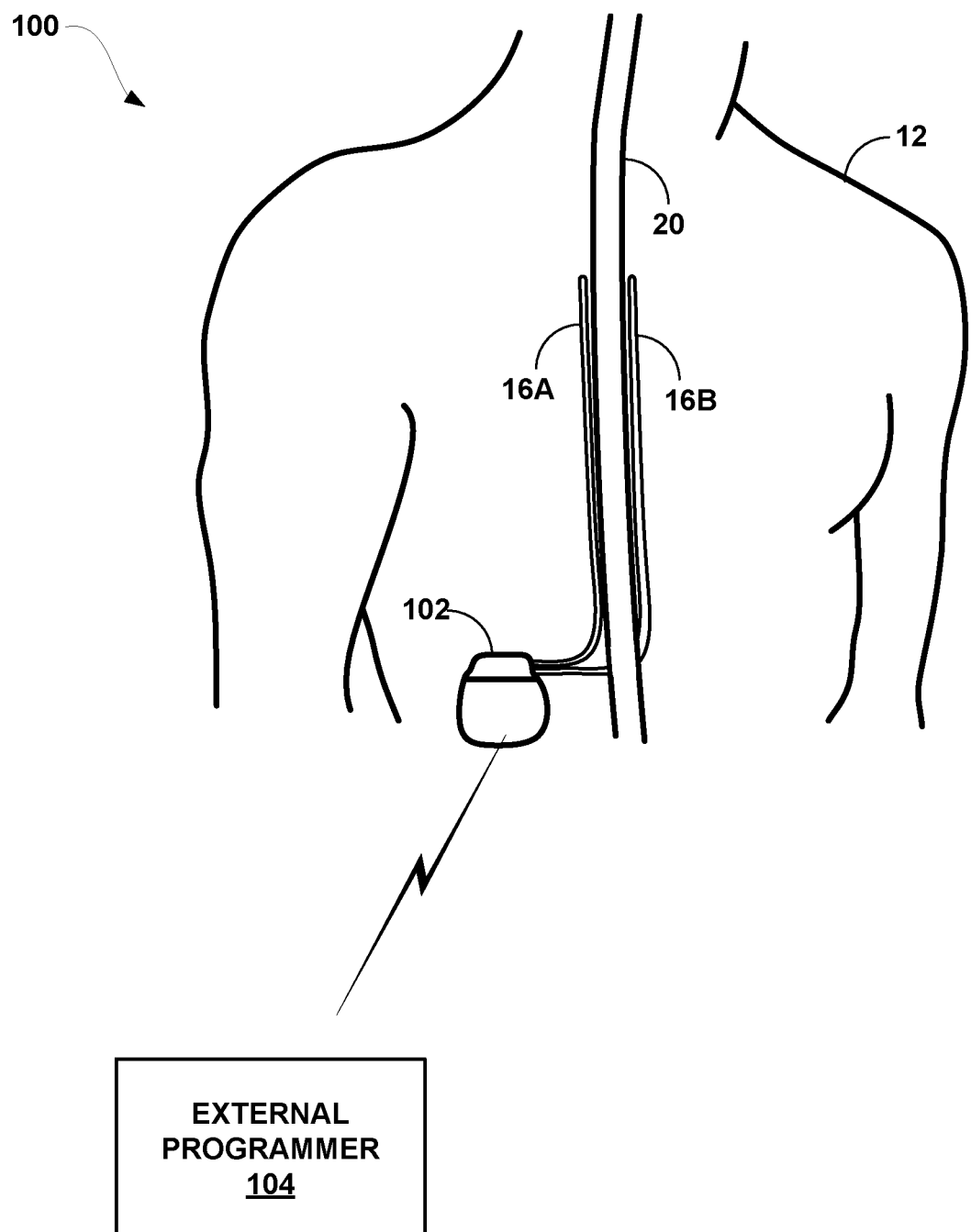
FIG. 1 is a conceptual diagram illustrating an example system that includes a medical device programmer and an implantable medical device (IMD) configured to deliver spinal cord stimulation (SCS) therapy according to the techniques of the disclosure.

In some examples, the disclosure describes example medical devices, systems, and techniques for automatically adjusting electrical stimulation therapy delivered to a patient to prevent or reduce the occurrence of evoked action potentials in tissue of the patient. For example, a medical device system may be configured to determine that electrical stimulation therapy being delivered to a patient according to a set of stimulation parameter values evokes an action potential in a tissue of a patient, e.g., by sensing the evoked compound action potentials in a tissue of the patient via one or more sensors. Based on the determination, the medical device system may be configured to adjust one or more of the stimulation parameter values defining the electrical stimulation therapy delivered to the patient to identify a set of therapy parameters values that do not evoke action potentials in a tissue of the patient when delivered.

Implantable medical devices (IMDs) may provide electrical stimulation therapy to treat various diseases or perform pain relief in the patient. In certain situations, the electrical stimulation therapy causes electrical charge to accrue in the tissue of the patient. This build-up of electrical charge may evoke an action potential in the nervous tissue of the patient. The action potential, a short-lasting event in which the electrical membrane potential of a cell rapidly rises and falls, may cause propagation of the electrical stimulation along the spinal cord to the brain, causing unwanted side effects, such as paresthesia or discomfort in the patient. A clinician may manually configure the one or more parameters defining the electrical stimulation therapy in a clinical visit to prevent evoking action potentials. However, over time, impedance changes in the electrical path through which the IMD delivers the electrical stimulation, movement of the leads of the IMD, and/or changes in the position or posture of the patient (among other reasons) may change the effect of the electrical stimulation therapy such that the delivered electrical stimulation therapy undesirably evokes action potentials in the tissue of the patient.

According to some examples of the disclosure, the described systems, devices, and techniques may be employed to prevent delivery of electrical stimulation that evoke action potentials in a tissue of the patient while still maintaining efficacious therapy. For example, a medical device system may be configured to determine that electrical stimulation therapy being delivered to a patient according to a set of stimulation parameter values evokes an action potential in a tissue of a patient, e.g., by sensing the evoked compound action potentials in a tissue of the patient via one or more sensors. As referred to herein, a compound action potential is a summation of a plurality of individual action potentials, wherein, due to the small magnitude of an individual action potential, the individual action potential may be difficult to accurately measure.

Based on the determination, the medical device system may be configured to adjust one or more of the stimulation parameter values defining the electrical stimulation therapy delivered to the patient to identify a set of therapy parameter values that do not evoke action potentials in a tissue of the patient when delivered.

As described above, in some examples, to adjust the electrical stimulation therapy, the medical device system may deliver a series of electrical pulses in which the amplitude of the respective pulses is increased, e.g., by ramping up the amplitude value of the respective pulses. The initial stimulation pulse may have an amplitude such that the delivered stimulation is below the activation threshold and does not evoke action potential in the tissue of a patient. While the series of pulses is delivered to the patient, the medical device system may monitor the patient to determine when a compound action potential is evoked by a stimulation pulse. The medical device system may then reduce the amplitude the stimulation to a value below the amplitude of the stimulation pulse that first evoked an action potential in the tissue of the patient, e.g., by a predetermined percentage or to the value of one of the preceding stimulation pulses in the series of delivery pulses. The medical device may then resume delivery of the electrical stimulation to the patient according to the adjusted amplitude value. In this manner, the medical device system may maintain the delivery of electrical stimulation to a patient that is below the activation threshold of the tissue such that compound action potentials are not evoked in the tissue (e.g., except for brief occurrences of evoked action potentials that may trigger the parameter adjustment), while also delivering therapy at a relatively high intensity.

The above is one example way to adjust therapy parameters based on an action potential being evoked. However, the techniques described in this disclosure are not limited to the above examples, and there may be additional ways in which evocation of an action potential may be used to adjust therapy parameters.

For instance, as part of normal therapy, the medical device may deliver alternating groups of pulses, where a group of pulses having a first amplitude is followed by a group of one or more pulses having a second amplitude, which are followed by a group of pulses having the first amplitude and so forth. The second amplitude is greater than the first amplitude. If the medical device, in response to delivery of a pulse having the second amplitude, determines that the action potential is evoked, the medical device may adjust the second amplitude downwards until the adjusted second amplitude is less than or equal to the activation threshold (e.g., until delivery of pulses having the adjusted second amplitude does not cause an action potential to be evoked).

The medical device may reduce the first amplitude to an adjusted first amplitude based on the adjusted second amplitude. For example, the adjusted first amplitude may be a factor of the adjusted second amplitude (e.g., 0.8*adjusted second amplitude). As another example, the medical device may reduce the first amplitude, to generate the adjusted first amplitude, by the same amount that the medical device reduced the second amplitude to generate the adjusted second amplitude. As another example, the medical device may reduce the first amplitude, to generate the adjusted first amplitude, by the same proportion that the medical device reduced the second amplitude to generate the adjusted second amplitude.

If the medical device, in response to delivery of a pulse having the second amplitude, determines that the action potential is not evoked, the medical device may adjust the second amplitude upwards until the adjusted second amplitude is greater than or equal to the activation threshold (e.g., until delivery of pulses having the adjusted second amplitude evokes an action potential). The medical device may increase the first amplitude to an adjusted first amplitude based on the adjusted second amplitude. For example, the adjusted first amplitude may be a factor of the adjusted second amplitude (e.g., 0.8*adjusted second amplitude). As another example, the medical device may increase the first amplitude, to generate the adjusted first amplitude, by the same amount that the medical device increased the second amplitude to generate the adjusted second amplitude. As another example, the medical device may increase the first amplitude, to generate the adjusted first amplitude, by the same proportion that the medical device increased the second amplitude to generate the adjusted second amplitude.

In this manner, the pulses having the second amplitude can be used to titrate the amplitude of the pulses having the first amplitude. Such techniques may allow for therapy adjustment that results in the amplitude for the stimulation pulses that is effective at providing therapy and efficient at power consumption, while potentially minimizing patient discomfort using a closed-loop technique. In this manner, the example techniques may address issues related to identifying the appropriate amplitude for stimulation pulses while ensuring effective therapy.

For instance, the frequency of the pulses having the first amplitude may be in the 10 kHz range, where stimulation may be effective at pain relief without the patient feeling the stimulation. The evocation of an action potential may correlate with the patient feeling the stimulation, or the patient feeling the stimulation may result in an action potential being evoked. In examples where a medical device delivers stimulation pulses having a frequency in the 10 kHz range, if the amplitude of the stimulation pulse is greater than an activation threshold to evoke an action potential, the patient may experience discomfort.

Accordingly, the amplitude of the stimulation pulses tends to be less than the activation threshold. However, because the amplitude of the stimulation pulses is less than the activation threshold, setting the amplitude so that the therapy is highly effective may be challenging as it may be difficult to determine how far below the activation threshold the amplitude is to be set, especially as the patient changes posture, as the efficacy of the stimulation may change with patient movement.

In some example techniques described in this disclosure, by intermingling pulses having a second amplitude with pulses having the first amplitude, the pulses having the second amplitude may be used to evoke an action potential (e.g., so that the patient can feel the stimulation), and then used to adjust the first amplitude. For example, with 10 kHz stimulation, every $200^{th}$ pulse may be at the second amplitude, and the other pulses may be at the first amplitude. In this example, a pulse having the second amplitude is intermingled with sequential groups of 200 pulses having the first amplitude (e.g., a first group of 200 pulses having the first amplitude is followed by a pulse having the second amplitude, which is followed by a second group of 200 pulses having the first amplitude and so forth).

The pulses having the second amplitude would be felt by the patient as 50 Hz stimulation, a frequency at which the patient may not feel discomfort. However, the pulses having the second amplitude may evoke an action potential. The medical device may sense the action potential to titrate the amplitude of the first pulses. For example, if an action potential is evoked, the medical device may reduce the second amplitude to an adjusted second amplitude. The first and second amplitudes may be set relative to one another. For example, if the medical device reduces the second amplitude by a certain percentage or certain voltage, the medical device may reduce the first amplitude by the same percentage or voltage. As an example, the lower amplitude higher frequency pulses may be delivered at a certain percentage below the higher amplitude pulse (e.g., 80% of the higher amplitude).

The medical device may keep adjusting the second amplitude lower until the adjusted second amplitude is equal to or less than the activation threshold (e.g., at or below the amplitude that causes an action potential to be evoked). The medical device may then adjust the first amplitude to an adjusted first amplitude based on the adjusted second amplitude. For example, the medical device may multiply the amplitude level of the adjusted second amplitude by a certain percentage (e.g., amplitude level of adjusted first amplitude equals 0.8*amplitude level of adjusted second amplitude).

In this example, prior to the adjustment, the patient may not experience any discomfort because pulses having the second amplitude, even if they evoke an action potential, are delivered at a relatively low frequency (e.g., 50 Hz), whereas patients may experience discomfort if pulses having the first amplitude evoked an action potential because of the relative high frequency of these pulses. When an adjustment event triggers the medical device to adjust therapy (for reasons described in more detail), although the patient may not be experiencing discomfort from the delivery of the pulses having the second amplitude that evoke an action potential, there may be potential benefits of adjusting the amplitudes of the pulses. For example, the first amplitude may be greater than necessary for delivering effective therapy, resulting in the medical device consuming more power than needed. By reducing the first amplitude, the medical device may still deliver effective therapy but consume less power. Also, the first amplitude may be close to the activation threshold, and there may be benefit in further reducing the first amplitude away from the activation threshold to minimize the possibility that the high frequency pulses evoke an action potential, which may cause the patient discomfort.

The medical device, in some examples, may use the evocation of action potentials to increase the first amplitude. For example, during delivery of therapy, the efficacy of the therapy may reduce for various reasons (e.g., change in lead impedance, movement of lead, etc.). In such examples, the amplitude of the high frequency therapy may be insufficient and should be increased. However, the amplitude should not be increased so high as to cause discomfort.

In response to an adjustment triggering event, the medical device may determine whether an action potential was evoked after delivery of one or more pulses having the second amplitude. If an action potential is not evoked, then it may be possible that the amplitude level of the first pulses having the first amplitude is less than the level at which more effective treatment may be delivered.

The medical device may increase the second amplitude to an adjusted second amplitude until the adjusted second amplitude is greater than or equal to the activation threshold (e.g., at or above the amplitude that causes an action potential to be evoked). Similar to above, the medical device may increase the first amplitude to an adjusted first amplitude based on the adjusted second amplitude (e.g., first adjusted amplitude equals 80% of the second adjusted amplitude). Because pulses having the second amplitude are delivered at a relatively low frequency, the evoking of an action potential may not cause the patient discomfort. Also, by keeping the adjusted first amplitude at a certain level lower than adjusted second amplitude, the adjusted first amplitude may be less than the activation threshold, which may result in the patient experiencing little to no discomfort from the high frequency pulses.

In examples where the medical device increased the second amplitude to be greater than or equal to the activation threshold, if the increased second amplitude is greater than the activation threshold, the medical device may reduce the second amplitude until the adjusted second amplitude is approximately equal to the activation threshold (e.g., within ±5-10% of the activation threshold). Similarly, in examples where the medical device decreased the second amplitude to be less than or equal to the activation threshold, if the decreased second amplitude is less than the activation threshold, the medical device may increase the second amplitude until the adjusted second amplitude is approximately equal to the activation threshold (e.g., within ±5-10% of the activation threshold). In this manner, the second amplitude may be increased and decreased as necessary to maintain the second amplitude with a desired range of the activation threshold.

The pulses having the second amplitude that are delivered less frequently than pulses having the first amplitude may be used to evoke an action potential. However, the pulses having the second amplitude may be used to deliver therapy as well. As one example, the pulses having the second amplitude may include a wider pulse width (e.g., 400 microseconds) than the pulses having the first amplitude (e.g., less than 400 microseconds). As another example, the pulses having the second amplitude may be delivered using different electrodes than the pulses having the first amplitude, where electrodes used for delivering the pulses having the second amplitude are selected as electrodes that provide therapy for low frequency stimulation pulses.

After the medical device determines the first adjusted amplitude and the second adjusted amplitude, the medical device may deliver stimulation pulses having the first adjusted amplitude intermingled with one or more pulses having the second adjusted amplitude. The medical device may deliver stimulation therapy comprising pulses having the first adjusted amplitude and pulses having the second adjusted amplitude may be until trigger of another adjustment event, at which point the medical device may further adjust the amplitude levels if needed.

There may be various triggers for adjusting therapy parameters. In some examples, the adjustment of the therapy parameters by the medical device system, as described herein, may be initiated based on a trigger other than that of directly sensing evoked compound action potentials in the tissue of a patient. In some examples, a medical device system may be programmed to periodically perform such an adjustment, e.g., on a daily or weekly basis. In some examples, the adjustment may be triggered by the determination that the patient has transitioned from one posture to another and/or occupies a particular posture (e.g., a posture that is likely to result in the delivered electrical stimulation therapy evoking action potential in the tissue of the patient). In another example, the adjustment may be triggered based on the receipt of input from the patient indicating that he/she is experiencing paresthesia or another effect indicating that the delivered therapy is an evoked action potential in the tissue of the patient. In other examples, the adjustment is performed in response to a signal received from a sensor, such as an accelerometer, a pressure sensor, a bending sensor, a sensor configured to detect a posture of the patient, or a sensor configured to detect a respiratory function of patient. In yet another example, the adjustment is performed in response to a signal indicating an electrically-evoked compound action potential (eCAP) of the tissue of the patient.

In some examples, the system monitors a tissue of the patient for an action potential evoked by the delivery of the electrical stimulation therapy. Upon detecting the evoked compound action potential, the system may suspend delivery of the electrical stimulation therapy for an amount of time. Alternatively, or additionally, the system may reduce the amplitude of the electrical stimulation therapy prior to resuming the delivery of therapy to determine a set of electrical stimulation parameters that do not evoke a compound action potential. Alternatively, or additionally, the suspended therapy may be resumed based on patient or other user input, e.g., received patient input. The suspension of therapy may be initiated based on another one of the example triggers described herein other than that of directly sensing compound action potentials evoked by the delivery electrical stimulation therapy.

In some examples, following the time period over which the therapy delivery is suspended, the system may perform titration of one or more parameters defining the electrical stimulation therapy delivered to the patient to adjust the electrical stimulation therapy such that the electrical stimulation provides efficacious therapy to the patient (e.g., by providing pain relief) while remaining substantially below a threshold that evokes a compound action potential in the tissue of the patient (e.g., an amplitude having a magnitude 5%, 10%, 15%, or 20% below a threshold amplitude that evokes a compound action potential). Generally speaking, the lower the amplitude, the less risk of evoking compound action potentials in the tissue of the patient and the less power consumption by the medical device.

Furthermore, in some examples, rather than suspending therapy, the medical device may adjust the amplitude of the therapy parameters during the delivery of therapeutic stimulation pulses. For instance, in the above examples where the evocation of the action potential is used to adjust upwards or downwards the amplitude of the high frequency pulses, the medical device may adjust the amplitude during the delivery of therapy. However, in some cases, it may be possible that in the examples where pulses having a second amplitude are intermingled with pulses having a first amplitude, the therapy is suspended or reduced while determining the adjusted first amplitude. For instance, the medical device may only output pulses having the second amplitude, but with parameters such as pulse width (e.g., 400 microseconds) and frequency (e.g., 50 Hz) that still provide some level of therapy. The medical device may not output pulses having the first amplitude until after the medical device determines the adjusted second amplitude from which the medical device determines the adjusted first amplitude.

As used herein, titration of one or more electrical stimulation therapy parameter(s) may refer to the gradual adjustment of one or more electrical stimulation therapy parameters to determine a primary set of electrical stimulation therapy parameters for subsequent delivery. In some examples, this gradual adjustment is an incremental or decremental adjustment, such as with a step function. In other examples, the gradual adjustment is continuous adjustment that is a substantially smooth increase or decrease in the value of the parameter. In one example of titration, a system selects a plurality of different values for an electrical stimulation therapy parameter, such as a current amplitude or a voltage amplitude, and the system delivers electrical stimulation according to the each of the values for the electrical stimulation therapy parameter. The system determines the response of the patient to the electrical stimulation described by each of the values for the electrical stimulation parameter. In some examples, the system gradually increases the value for the electrical stimulation parameter. In other examples, the system gradually decreases the value for the electrical stimulation parameter. In yet further examples, the system selects randomized, non-ordered values for the electrical stimulation parameter. In this fashion, the system may test a plurality of different values to select a primary set of electrical stimulation therapy parameters for subsequent delivery to the patient. In some examples, a clinician may titrate, or instruct the system to titrate, one or more electrical stimulation therapy parameters to determine a primary set of electrical stimulation therapy parameters that describe an electrical stimulation therapy that has the greatest efficacy in treating one or more diseases of the patient, evokes the fewest side effects in the patient, or satisfies other criteria for the delivery of electrical stimulation therapy. In other examples, the system titrates one or more electrical stimulation therapy parameters to determine a primary set of electrical stimulation therapy parameters that describe an electrical stimulation therapy that does not evoke a compound action potential in the patient but effectively treats pain of the patient.

Example techniques of the disclosure may allow a medical device system to detect an evoked compound action potential occurring in a tissue of a patient during delivery of an electrical stimulation therapy, and in response to the detected compound action potential, adjust one or more parameters of a plurality of electrical stimulation therapy programs. Such an IMD system may allow a clinician to quickly configure a system for delivering electrical stimulation therapy to provide pain relief without paresthesia. For example, an IMD system as described herein may automatically titrate or adjust one or more parameters defining the electrical stimulation therapy during an initial or subsequent programming session to identify one or more sets of therapy parameter values (also referred to as a therapy program) without the need for patient feedback. Furthermore, because an IMD system as described herein provides for automatic titration of the one or more parameters, the IMD system may periodically perform such titration at home or at the request of a patient without the involvement of the clinician.

FIG. 1 is a conceptual diagram illustrating example system 100 that includes implantable medical device (IMD) 102 configured to deliver electrical stimulation therapy to patient 12. In the example shown in FIG. 1, IMD 102 is configured to deliver SCS therapy according to the techniques of the disclosure. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 100 includes an IMD 102, leads 16A, 16B, and external programmer 104 shown in conjunction with a patient 12, who is ordinarily a human patient. In the example of FIG. 1, IMD 102 is an implantable electrical stimulator that is configured to generate and deliver electrical stimulation therapy to patient 12 via electrodes of leads 16A, 16B, e.g., for relief of chronic pain or other symptoms. IMD 102 may be a chronic electrical stimulator that remains implanted within patient 12 for weeks, months, or even years. In other examples, IMD 102 may be a temporary, or trial, stimulator used to screen or evaluate the efficacy of electrical stimulation for chronic therapy. In one example, IMD 102 is implanted within patient 12, while in another example, IMD 102 is an external device coupled to percutaneously implanted leads. In some examples, IMD uses one or more leads, while in other examples, IMD 102 is leadless.

IMD 102 may be constructed of any polymer, metal, or composite material sufficient to house the components of IMD 102 (e.g., components illustrated in FIG. 2) within patient 12. In this example, IMD 102 may be constructed with a biocompatible housing, such as titanium or stainless steel, or a polymeric material such as silicone, polyurethane, or a liquid crystal polymer, and surgically implanted at a site in patient 12 near the pelvis, abdomen, or buttocks. In other examples, IMD 102 may be implanted within other suitable sites within patient 12, which may depend, for example, on the target site within patient 12 for the delivery of electrical stimulation therapy. The outer housing of IMD 102 may be configured to provide a hermetic seal for components, such as a rechargeable or non-rechargeable power source. In addition, in some examples, the outer housing of IMD 102 may be selected from a material that facilitates receiving energy to charge the rechargeable power source.

Electrical stimulation energy, which may be constant current or constant voltage based pulses, for example, is delivered from IMD 102 to one or more target tissue sites of patient 12 via one or more electrodes (not shown) of implantable leads 16A and 16B (collectively "leads 16"). In the example of FIG. 1, leads 16 carry electrodes that are placed adjacent to the target tissue of spinal cord 20. One or more of the electrodes may be disposed at a distal tip of a lead 16 and/or at other positions at intermediate points along the lead. Leads 16 may be implanted and coupled to IMD 102. The electrodes may transfer electrical stimulation generated by an electrical stimulation generator in IMD 102 to tissue of patient 12. Although leads 16 may each be a single lead, lead 16 may include a lead extension or other segments that may aid in implantation or positioning of lead 16. In some other examples, IMD 102 may be a leadless stimulator with one or more arrays of electrodes arranged on a housing of the stimulator rather than leads that extend from the housing. In addition, in some other examples, system 100 may include one lead or more than two leads, each coupled to IMD 102 and directed to similar or different target tissue sites.

The electrodes of leads 16 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. Ring electrodes arranged at different axial positions at the distal ends of lead 16 will be described for purposes of illustration.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

The therapy parameters for a therapy program (also referred to herein as a set of electrical stimulation parameter values) that controls delivery of stimulation therapy by IMD 102 through the electrodes of leads 16 may include information identifying which electrodes have been selected for delivery of stimulation according to a stimulation program, the polarities of the selected electrodes, i.e., the electrode combination for the program, and voltage or current amplitude, pulse rate, and pulse width of stimulation delivered by the electrodes. Delivery of stimulation pulses will be described for purposes of illustration.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 12.

In some examples, lead 16 may include one or more sensors configured to allow IMD 102 to monitor one or more parameters of patient 12. The one or more sensors may be provided in addition to, or in place of, therapy delivery by lead 16.

IMD 102 is configured to deliver electrical stimulation therapy to patient 12 via selected combinations of electrodes carried by one or both of leads 16, alone or in combination with an electrode carried by or defined by an outer housing of IMD 102. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 20, such as within an intrathecal space or epidural space of spinal cord 20, or, in some examples, adjacent nerves that branch off of spinal cord 20. Leads 16 may be introduced into spinal cord 20 in via any suitable region, such as the thoracic, cervical or lumbar regions. Stimulation of spinal cord 20 may, for example, prevent pain signals from traveling through spinal cord 20 and to the brain of patient 12. Patient 12 may perceive the interruption of pain signals as a reduction in pain and, therefore, efficacious therapy results.

IMD 102 generates and delivers electrical stimulation therapy to a target stimulation site within patient 12 via the electrodes of leads 16 to patient 12 according to one or more therapy programs. A therapy program defines values for one or more parameters that define an aspect of the therapy delivered by IMD 102 according to that program. For example, a therapy program that controls delivery of stimulation by IMD 102 in the form of pulses may define values for voltage or current pulse amplitude, pulse width, and pulse rate for stimulation pulses delivered by IMD 102 according to that program.

Moreover, in some examples, IMD 102 delivers electrical stimulation therapy to patient 12 according to multiple therapy programs, which may be stored as a therapy program group. For example, as described below, in some examples, IMD 102 may deliver different pulses of electrical stimulation signal via respective electrode combinations, and each of the electrode combinations may be associated with a respective therapy program. The therapy programs may be stored as a group, such that when IMD 102 generates and delivers electrical stimulation therapy via a selected group, IMD 102 delivers electrical stimulation signal via two or more therapy programs.

A user, such as a clinician or patient 12, may interact with a user interface of an external programmer 104 to program IMD 102. Programming of IMD 102 may refer generally to the generation and transfer of commands, programs, or other information to control the operation of IMD 102. In this manner, IMD 102 may receive the transferred commands and programs from programmer 104 to control stimulation therapy. For example, external programmer 104 may transmit therapy programs, stimulation parameter adjustments, therapy program selections, therapy program group selections, user input, or other information to control the operation of IMD 102, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy. In general, a physician or clinician programmer may support selection and generation of programs by a clinician for use by IMD 102, whereas a patient programmer may support adjustment and selection of such programs by a patient during ordinary use. In other examples, external programmer 104 may be included, or part of, an external charging device that recharges a power source of IMD 102. In this manner, a user may program and charge IMD 102 using one device, or multiple devices.

As described herein, information may be transmitted between external programmer 104 and IMD 102. Therefore, IMD 102 and programmer 104 may communicate via wireless communication using any techniques known in the art. Examples of communication techniques may include, for example, radiofrequency (RF) telemetry and inductive coupling, but other techniques are also contemplated. In some examples, programmer 104 may include a communication head that may be placed proximate to the patient's body near the IMD 102 implant site in order to improve the quality or security of communication between IMD 102 and programmer 104. Communication between programmer 104 and IMD 102 may occur during power transmission or separate from power transmission.

In some examples, IMD 102, in response to commands from external programmer 104, delivers electrical stimulation therapy according to a plurality of electrical stimulation therapy programs to a target tissue site of the spinal column 20 of patient 12 via electrodes (not depicted) on leads 16. In some examples, IMD 102, in response to commands from external programmer 104, titrates one or more parameters defining the plurality of electrical stimulation therapy programs, for example, a voltage amplitude (for voltage controlled devices), a current amplitude (for current-controlled devices), a pulse width, or a pulse frequency, to deliver electrical stimulation of gradually increasing strength. As described further below, the titration may be used to identify a set of therapy parameter values for an electrical stimulation therapy that does not evoke action potentials in the tissue of a patient when delivered but that also provides for efficacious treatment of patient pain.

During delivery of therapy, IMD 102 may be configured to adjust therapy parameters in response to a trigger for adjusting therapy. One example of an electrical stimulation therapy program is an electrical stimulation therapy program that causes IMD 102 to deliver stimulation therapy that includes a first set of plurality of pulses having a first amplitude, and a second set of plurality of pulses having a second amplitude greater than the first amplitude. One or more pulses of the second set of plurality of pulses are intermingled with sequential groups of pulses of the first set of plurality of pulses (e.g., a group of pulses having a first amplitude is followed by one or more pulses having a second amplitude, which are followed by a group of pulses having the first amplitude, and so forth).

After delivering a stimulation pulse having the second amplitude, IMD 102 may determine whether an action potential is evoked. If IMD 102 determines that an action potential is evoked, IMD 102 may adjust the second amplitude to an adjusted second amplitude until the adjusted second amplitude is less than or equal to an activation threshold, where delivery of pulses having an amplitude level less than the activation threshold does not cause an action potential to be evoked. If IMD 102 determines that an action potential is not evoked after delivering a stimulation pulse having the second amplitude, IMD 102 may adjust the second amplitude to an adjusted second amplitude until the adjusted second amplitude is greater than or equal to the activation threshold, where delivery of pulses having an amplitude level greater than or equal to the activation threshold causes an action potential to be evoked.

The difference in the amplitude level of the first amplitude and the second amplitude may be set, or the first amplitude may be set ratio of the second amplitude. IMD 102 may use the set difference or set ratio to adjust the first amplitude to an adjusted first amplitude based on the adjusted second amplitude. IMD 102 may then deliver stimulation therapy based at least on the adjusted first amplitude. For example, IMD 102 may deliver stimulation therapy that includes a third set of pulses having the first adjusted amplitude, and a fourth set of pulses having the second adjusted amplitude, where one or more pulses having the second adjusted amplitude are intermingled with sequential groups of pulses having the first adjusted amplitude.

In some examples, the target tissue is a tissue of the spinal column 20 of patient 12. As one example, the target tissue may be a tissue of a dorsal column of the spinal column 20 of patient 12. In other examples, the target tissue is a nerve tissue of patient 12 or a muscle tissue of patient 12.

During delivery of electrical stimulation therapy defined by one or more electrical stimulation programs, IMD 102, via the electrodes interposed on leads 16, senses target tissue site of the spinal column 20 of patient 12 to measure the electrical activity of the target tissue site. IMD 102 senses when electrical stimulation therapy defined by the one or more electrical stimulation programs evokes a compound action potential in the target tissue site of patient 12. In some examples, IMD 102 receives a signal indicative of the compound action potential from one or more sensors internal or external to patient 12. Such an example signal may include a signal indicating an electrically-evoked compound action potential (eCAP) of the tissue of the patient 12. Examples of the one or more sensors include one or more sensors configured to measure an compound action potential of the patient 12, or a side effect indicative of a compound action potential. For example, the one or more sensors may be an accelerometer, a pressure sensor, a bending sensor, a sensor configured to detect a posture of patient 12, or a sensor configured to detect a respiratory function of patient 12. However, in other examples, external programmer 104 receives a signal indicating a compound action potential in the target tissue of patient 12 and transmits a notification to IMD 102.

In response to sensing an evoked compound action potential, IMD 102 adjusts at least one electrical stimulation therapy program of the plurality of electrical stimulation therapy programs. For example, IMD 102 selects a value for the one or more parameters defining the electrical stimulation therapy such that delivery of the electrical stimulation therapy does not evoke a compound action potential in the patient. As another example, IMD 102 halts delivery of the electrical stimulation therapy. In yet another example, IMD 102 selects a different electrical stimulation therapy program of the plurality of electrical stimulation therapy programs for defining the delivery of electrical stimulation therapy to patient 12. As yet another example, IMD 102 keeps delivering therapy that includes pulses having a higher amplitude relative to other pulses in the therapy, where the pulses having the higher amplitude are delivered less frequently. IMD 102 may adjust the amplitude level of these pulse having the higher amplitude until a compound action potential is evoked if increasing the amplitude of therapy or is not evoked if decreasing the amplitude of therapy, and adjust the amplitude level of the other pulses based on the adjustment to the pulses having the higher amplitude.

In some examples, a patient or clinician uses external programmer 104 to instruct IMD 102 to perform titration or other adjustment to the one or more parameters defined by an electrical stimulation therapy programs to calibrate the electrical stimulation therapy delivered by IMD 102. For example, a clinician, via external programmer 104, may perform such a titration to configure IMD 102 for delivery of therapy in an outpatient or post-implantation setting. Similarly, patient 12 may require an adjustment of the parameters describing the electrical stimulation therapy programs, i.e., because patient 12 is experiencing side effects of the electrical stimulation therapy. In this example, patient 12, via external programmer 104, performs such a titration to reconfigure IMD 102 for delivery of therapy. In another example, during subsequent use by patient 12, IMD 102 periodically monitors the target tissue site of patient 12 for an evoked compound action potential and adjusts the plurality of electrical stimulation therapy programs defining the electrical stimulation therapy in response to the evoked compound action potential. Such an evoked compound action potential may arise over time due to impedance changes in the IMD 102, movement of the leads of the IMD, and changes in the position of IMD 102, and indicate a need for recalibration of the electrical stimulation therapy delivered by IMD 102.

In response to determining that an evoked compound action potential occurs, IMD 102 suspends delivery of the electrical stimulation therapy to stop the compound action potential. In one example, after suspending delivery of the electrical stimulation therapy for a predetermined amount of time, IMD 102 resumes delivery of the electrical stimulation therapy. For example, evoked action potentials in patient 112 may result in significant but transient side effects, such as paresthesia, respiratory distress (i.e., coughing), or falling. Instead of attempting to determine a new amplitude for the electrical stimulation while the transient side effects are occurring, IMD 102 suspends therapy to allow the transient side effects to dissipate and resumes therapy after the transient side effects have subsided. In some examples, if after several attempts to resume delivery of electrical stimulation fail (i.e., because compound action potentials are detected or because the side effects are still present), IMD 102 may determine that the side effects are a new steady state for patient 112 given the present amplitude of electrical stimulation therapy. Accordingly, IMD 102 may perform titration, as described below, of one or more parameters describing the electrical stimulation therapy to determine an electrical stimulation that, when delivered according to a new set of electrical stimulation parameters, does not evoke an action potential in the tissue of patient 112.

In another example, after the predetermined amount of time, IMD 102, via electrodes of leads 16, delivers electrical stimulation therapy according to one or more reduced parameters, such as a reduced amplitude. IMD 102 senses, via electrodes of leads 16, an electrical parameter of the target tissue site of patient 12 to determine whether the electrical stimulation therapy according to the one or more reduced parameters continues to evoke a compound action potential. Upon determining that the target tissue site no longer exhibits a compound action potential, IMD 102 resumes delivery of the electrical stimulation therapy according to the one or more reduced parameters. Upon determining that the target tissue site continues to exhibit a compound action potential, IMD 102 suspends the electrical stimulation therapy for another unit of the predetermined amount of time. Typically, the predetermined amount of time is in the order of minutes, e.g., approximately 1 minute, approximately 10 minutes, approximately 30 minutes, etc.

After the predetermined amount of time, IMD 102 delivers electrical stimulation according to one or more parameters having further reduced magnitudes, and again determines whether the electrical stimulation according to one or more parameters having further reduced magnitudes continues to evoke a compound action potential. Upon determining that no such compound action potential is evoked, IMD 102 gradually increases the magnitude of the one or more parameters, delivers electrical stimulation according to the one or more parameters, and determines a point at which the electrical stimulation evokes a compound action potential to determine a threshold at which the magnitude of the one or more parameters defining the electrical stimulation therapy evokes a compound action potential. At this point, IMD 102 may reduce the magnitude of the one or more parameters by a percentage or ratio substantially below the magnitude of the one or more parameters that evokes a compound action potential. For example, the percentage or value may be 90%, 80%, 60%, or 40% of the magnitude of the one or more parameters that evoked the compound action potential, etc. IMD 102 delivers electrical stimulation therapy according to one or more parameters substantially below the threshold that evokes a compound action potential in the patient.

As described herein, in some examples, upon resuming the delivery of electrical stimulation therapy, IMD 102 may titrate or otherwise adjust one or more electrical stimulation parameters of the previously suspended therapy to identify a set of therapy parameters that do not evoke compound action potentials in the tissue of the patient while maintaining efficacious therapy.

In yet another example, rather than suspending delivery of therapy, even if an action potential is evoked, IMD 102 may keep delivering therapy. For instance, in some examples, IMD 102 may deliver pulses having a second amplitude intermingled with pulses having a first amplitude. The pulses having the second amplitude may evoke an action potential. However, the frequency of delivery of the pulses having the second amplitude may be sufficiently low that the patient does not experience much if any discomfort. For example, if action potentials are evoked at a relatively low frequency, the patient may not feel discomfort, but may feel discomfort when action potentials are evoked more frequently. IMD 102 may use the evocation of the action potential to titrate the amplitude of the higher frequency pulses (e.g., those having the first amplitude).

In some cases, the pulses having the second amplitude may also provide therapy in addition to being used for titrating the amplitude. For example, the pulses having the higher amplitude (e.g., second amplitude) and delivered less frequently (e.g., delivered at a lower frequency) may have a greater pulse width than the pulses having the lower amplitude (e.g., first amplitude) and delivered more frequency (e.g., delivered at a higher frequency), and may be delivered using different combination of electrodes.

The example techniques that intermingle pulses having different amplitudes in the stimulation therapy may allow for a better controlled and potentially faster technique to set the stimulation amplitude for the high frequency pulses (e.g., those that are not to evoke the action potential). For instance, IMD 102 may sense an evoked compound action potential (ECAPs) that is used to automatically set the amplitude correctly in real time by detecting the propagation of the action potential upon the spinal cord for the lower frequency pulses (e.g., pulses having the second amplitude that are delivered less frequently than pulses having the first amplitude). IMD 102 may include filters to filter the noise from the higher frequency pulses so that the sensing circuit is properly measuring the action potential caused by delivery of the lower frequency stimulation pulses having the second amplitude. As one example, sensing module 204 may include an electrical isolation (e.g., optical isolator or the like) between sensing module 2014 and stimulation generator 202 that filters the noise.

As another example, stimulation generator 202 may include a delay circuit that delays delivery of the pulses having the lower amplitude (e.g., first amplitude) but higher frequency after delivery of a pulse having the higher amplitude (e.g., second amplitude) but lower frequency. The delay of the delivery of the pulses having the lower amplitude/higher frequency would allow processor 210 sufficient time monitor for the action potential after delivery of the lower frequency pulse without noise from the higher frequency pulses disturbing the monitoring. As one example, the delay circuit may delay delivery of pulses having the lower amplitude/higher frequency by 1 to 5 milliseconds after delivery of a pulse having the higher amplitude/lower frequency.

In some examples, upon detecting an evoked compound action potential, IMD 102 automatically performs titration of one or more parameters defining the electrical stimulation therapy delivered to the patient to adjust the electrical stimulation therapy such that the electrical stimulation provides adequate therapy to the patient while remaining below a threshold that evokes a compound action potential in the tissue of the patient. In other words, upon detecting the evoked compound action potential, IMD 102 automatically titrates one or more parameters defining the plurality of electrical stimulation therapy programs, for example, a voltage amplitude (for voltage controlled devices), a current amplitude (for current-controlled devices), a pulse width, or a pulse frequency, to gradually reduce the magnitude of the one or more parameters defining the plurality of electrical stimulation therapy programs. Upon determining a value for the one or more parameters describing the electrical stimulation therapy that does not evoke a compound action potential in patient 12, IMD 102 selects that value for the one or more parameters and resumes delivery of the electrical stimulation therapy according to the new parameter set.

In the example of FIG. 1, IMD 102 described as performing a plurality of processing and computing functions. However, external programmer 104 instead may perform one, several, or all of these functions. In this alternative example, IMD 102 functions to relay sensed signals to external programmer 104 for analysis, and external programmer 104 transmits instructions to IMD 102 to adjust the one or more parameters defining the electrical stimulation therapy. For example, IMD 102 may relay the sensed signal indicative of an evoked compound action potential to external programmer 104. In response to the signal, external programmer 104 may instruct IMD 102 to halt delivery of electrical stimulation, select another electrical stimulation program of the plurality of electrical stimulation programs that defines the electrical stimulation therapy delivered to patient 12, or adjust one or more parameters defines the electrical stimulation therapy delivered to patient 12.

Accordingly, some examples of the disclosure allow a system 100 including an IMD 102 to detect an evoked compound action potential occurring in a tissue of a patient 12, and in response to the detected action potential, adjust one or more parameters defining the electrical stimulation therapy. System 100 may allow a clinician to quickly configure a system for delivering electrical stimulation therapy to provide pain relief without paresthesia. For example, a system 100 as described herein may automatically titrate or otherwise adjust one or more parameters defining the electrical stimulation therapy during configuration without the need for feedback from patient 12. Furthermore, because system 100 as described herein provides for automatic titration of the one or more parameters, system 100 may periodically perform such titration at home or at the request of patient 12 without the involvement of the clinician.

Figure 2:
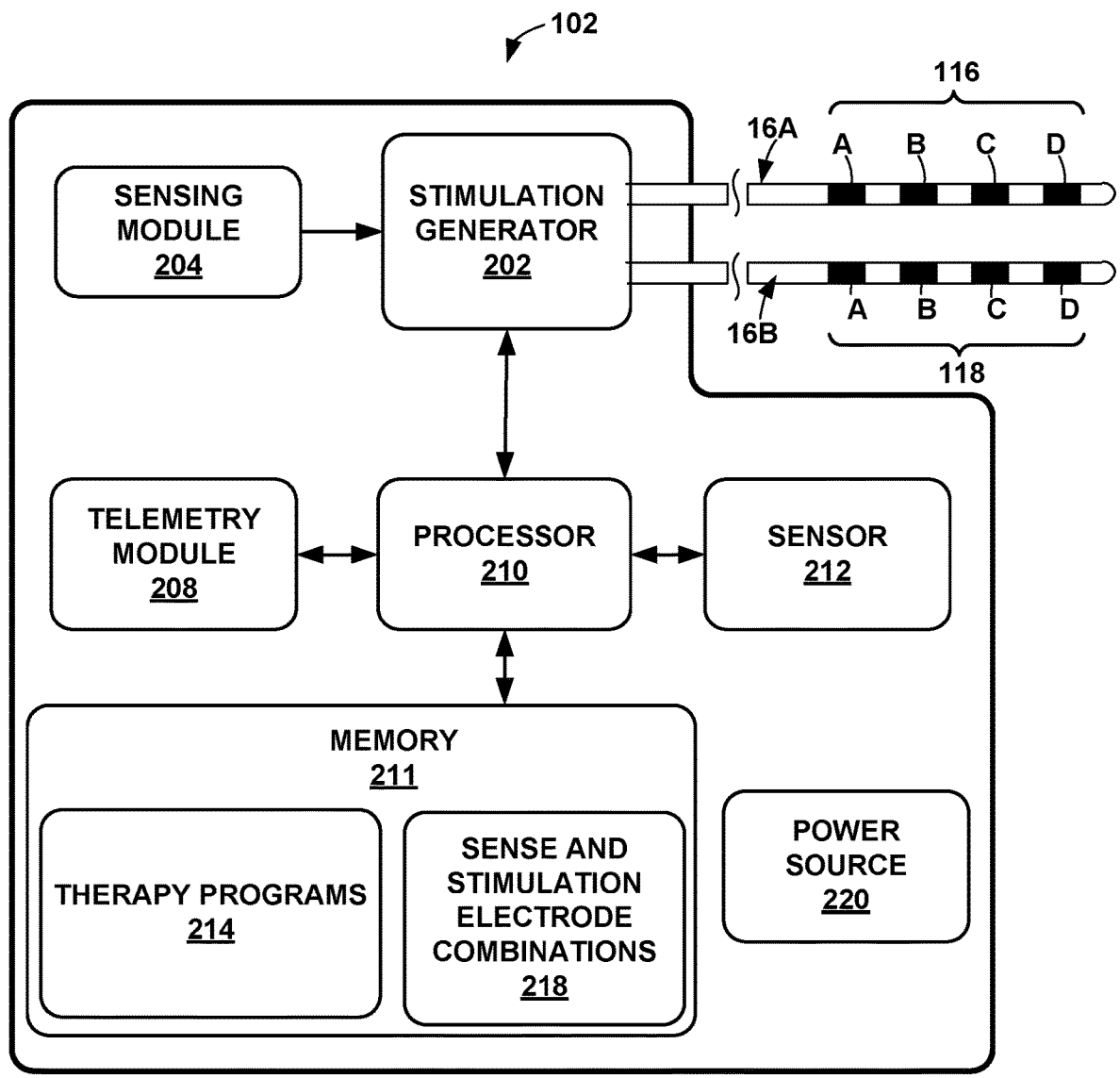
FIG. 2 is a block diagram of the example IMD of FIG. 1.

FIG. 2 is a block diagram of the example IMD 102 of FIG. 1. In the example shown in FIG. 2, IMD 102 includes processor 210, memory 211, stimulation generator 202, sensing module 204, telemetry module 208, sensor 212, and power source 220. Each of these modules may be or include electrical circuitry configured to perform the functions attributed to each respective module. For example, processor 210 may include processing circuitry, stimulation generator 202 may include switch circuitry, sensing module 204 may include sensing circuitry, and telemetry module 208 may include telemetry circuitry. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 102 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group include stimulation pulses that may be delivered together on an overlapping or non-overlapping (e.g., time-interleaved) basis.

Accordingly, in some examples, stimulation generator 202 generates electrical stimulation signals in accordance with the electrical stimulation parameters noted above. Other ranges of therapy parameter values may also be useful, and may depend on the target stimulation site within patient 12. While stimulation pulses are described, stimulation signals may be of any form, such as continuous-time signals (e.g., sine waves) or the like.

Processor 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 controls stimulation generator 202 according to therapy programs 214 stored in memory 211 to apply particular stimulation parameter values specified by one or more of programs, such as amplitude, pulse width, and pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 also controls stimulation generator 202 to generate and apply the stimulation signals to selected combinations of electrodes 116, 118. In some examples, stimulation generator 202 includes a switch module that couples stimulation signals to selected conductors within leads 16, which, in turn, deliver the stimulation signals across selected electrodes 116, 118. Such a switch module may be a switch array, switch matrix, multiplexer, or any other type of switching module configured to selectively couple stimulation energy to selected electrodes 116, 118 and to selectively sense bioelectrical neural signals of spine 20 with selected electrodes 116, 118.

In other examples, however, stimulation generator 202 does not include a switch module. In these examples, stimulation generator 202 comprises a plurality of pairs of voltage sources, current sources, voltage sinks, or current sinks connected to each of electrodes 116, 118 such that each pair of electrodes has a unique signal generator. In other words, in these examples, each of electrodes 116, 118 is independently controlled via its own signal generator (e.g., via a combination of a regulated voltage source and sink or regulated current source and sink), as opposed to switching signals between electrodes 116, 118.

Stimulation generator 202 may be a single channel or multi-channel stimulation generator. In particular, stimulation generator 202 may be capable of delivering a single stimulation pulse or multiple stimulation pulses at a given time via a single electrode combination or multiple stimulation pulses at a given time via multiple electrode combinations. In some examples, however, stimulation generator 202 may be configured to deliver multiple channels on a time-interleaved basis. For example, a switch module of stimulation generator 202 may serve to time divide the output of stimulation generator 202 across different electrode combinations at different times to deliver multiple programs or channels of stimulation energy to patient 12. In another example, the stimulation generator 202 may control the independent sources or sinks on a time-interleaved basis.

Electrodes 116, 118 on respective leads 16 may be constructed of a variety of different designs. For example, one or both of leads 16 may include two or more electrodes at each longitudinal location along the length of the lead, such as multiple electrodes at different perimeter locations around the perimeter of the lead at each of the locations A, B, C, and D. On one example, the electrodes may be electrically coupled to stimulation generator 202, e.g., switching circuitry of the stimulation generator, via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 16. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from IMD 102 and may communicate with processor 210 via wired or wireless communication techniques. Example bioelectrical signals include, but are not limited to, a signal generated from local field potentials within one or more regions of spine 20.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 102 may include additional sensors within the housing of IMD 102 and/or coupled via one of leads 16 or other leads. In addition, IMD 102 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient).

Telemetry module 208 supports wireless communication between IMD 102 and an external programmer 104 or another computing device under the control of processor 210. Processor 210 of IMD 102 may receive, as updates to programs, values for various stimulation parameters such as amplitude and electrode combination, from programmer 104 via telemetry module 208. The updates to the therapy programs may be stored within therapy programs 214 portion of memory 211. Telemetry module 208 in IMD 102, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 102 with programmer 104. Accordingly, telemetry module 208 may send information to external programmer 104 on a continuous basis, at periodic intervals, or upon request from IMD 102 or programmer 104.

Power source 220 delivers operating power to various components of IMD 102. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, processor 210 of IMD 102 receives, via telemetry module 208, instructions to deliver electrical stimulation therapy according to the one or more electrical stimulation therapy programs to a target tissue site of the spinal column 20 of patient 12 via a plurality of electrode combinations of electrodes 116, 118 of leads 16 and/or a housing of IMD 102. In some examples, processor 210 of IMD 102, in response to commands from external programmer 104, titrates one or more parameters defining the plurality of electrical stimulation therapy programs, for example, a voltage amplitude (for voltage controlled devices), a current amplitude (for current-controlled devices), a pulse width, or a pulse frequency, to deliver electrical stimulation of gradually increasing strength.

In some examples, processor 210 of IMD 102, in response to commands from external programmer 104, titrates one or more parameters defining the plurality of electrical stimulation therapy programs, for example, a voltage amplitude (for voltage controlled devices), a current amplitude (for current-controlled devices), a pulse width, or a pulse frequency, to deliver electrical stimulation that includes one or more pulses having a higher amplitude intermingled with groups of pulses having a lower amplitude, where the one or more pulses having the higher amplitude are delivered less frequently than the pulses having the lower amplitude. For example, the group of pulses having the lower amplitude include more pulses than the one or more pulses having the higher amplitude that are intermingled with the groups of pulses having the lower amplitude.

Processor 210 of IMD 102 controls stimulation generator 202 to deliver electrical stimulation therapy according to the one or more electrical stimulation therapy programs to patient 12 via a plurality of electrode combinations of electrodes 116, 118 of leads 16 at a high frequency, such as a frequency selected from a range of approximately 1,000 Hertz to approximately 10,000 Hertz. In other examples, processor 210 of IMD 102 delivers electrical stimulation therapy according to a plurality of lower-frequency electrical stimulation therapy programs to the patient 12 via a plurality of electrode combinations of electrodes 116, 118 of leads 16 and on a time-interleaved basis to effectively deliver combined, higher-frequency electrical stimulation to a target tissue site. Techniques for delivering such a combined, higher-frequency electrical stimulation to a target tissue site are described in more detail in U.S. Prov. App. No. 62/378,544 to Nathan Torgerson, entitled "DELIVERY OF INDEPENDENT INTERLEAVED PROGRAMS TO PRODUCE HIGHER-FREQUENCY ELECTRICAL STIMULATION THERAPY" and filed on Aug. 23, 2016.

In one example, the electrical stimulation signal comprises of one or more electrical pulses (e.g., a pulse train), wherein each pulse has a pulse width in a range of 2 microseconds to 833 microseconds. In a further example, each pulse has a pulse width of about 20 microseconds to about 60 microseconds. In one example, the electrical stimulation signal comprises of one or more electrical pulses (e.g., a pulse train), wherein each pulse has a pulse width in a range of 30 microseconds to 60 microseconds. In one example, the electrical stimulation signal comprises of one or more electrical pulses (e.g., a pulse train), wherein each pulse has a pulse width of approximately 50 microseconds. In one example, the electrical stimulation signal comprises of one or more electrical pulses (e.g., a pulse train), wherein each pulse has a pulse width of approximately 60 microseconds. In one example, the electrical stimulation signal comprises pulses having a first amplitude and a first pulse width (e.g., 100 microseconds), and pulses having a second amplitude greater than the first amplitude. The pulses having the second amplitude may also comprise a second, different pulse width (e.g., 400 microseconds), but not necessarily in all examples.

In some examples, IMD 102 delivers the pulses of the electrical stimulation signal via different electrode combinations of two or more of electrodes 116A-116D and 118A-118D and a housing of IMD 102. For example, IMD 102 may alternate delivery of pulses between two or more different electrode combinations, or may otherwise interleave the pulses using two or more electrode combinations in any suitable order. In one example, each electrode combination comprises at least one electrode functioning as an anode and at least one other electrode functioning as a cathode, and these electrodes are unique to the electrode combination in that the same electrodes are not used in other electrode combinations that are used to delivery time-interleaved stimulation pulses.

In some examples, the electrical stimulation therapy signal may have a frequency range of approximately 50-200 Hertz. However, in other examples, the electrical stimulation therapy has a frequency greater than approximately 1 Hertz in some examples, greater than 1,200 Hertz in some examples, greater than 1,500 Hertz in other examples, greater than 5,000 Hertz in other examples, or greater than 10,000 Hertz in still other examples. When higher frequencies are used in a system using electrically-evoked compound action potentials (ECAPs) to determine if compound action potentials are present, it may be necessary to briefly suspend the delivery of electrical stimulation and deliver a single pulse at a lower amplitude (or a burst of pulses having a lower frequency) to detect the presence of eCAP. However, suspending therapy in all cases may not be necessary, such as in examples where eCAP is detected due to pulses that are delivered at a relatively low frequency (e.g., 50 Hz), such as where these pulses are intermingled with groups of pulses having a lower amplitude delivered at a higher frequency. Additionally, the electrical stimulation therapy signal may have a frequency of less than approximately 20,000 Hertz in some examples, less than 10,000 Hertz in other examples, less than 5,000 Hertz in other examples, less than 1,500 Hertz in other examples, less than 1,000 Hertz in other examples, or less than 200 Hertz in still other examples.

During delivery of electrical stimulation therapy according to the one or more electrical stimulation programs, processor 210, via electrodes 116, 118 interposed along leads 16, senses the target tissue site of the spinal column 20 of patient 12 and measures the electrical activity of the target tissue site. For example, electrodes 116, 118 may sense an electrically-evoked compound action potential (eCAP) of the tissue of the patient. Upon detecting that the electrical stimulation therapy according to the one or more electrical stimulation programs evokes a compound action potential in the target tissue site of patient 12, processor 204 adjusts at least one electrical stimulation therapy program of the plurality of electrical stimulation therapy programs.

In an alternative example, processor 204 receives a signal indicative of an evoked compound action potential from one or more sensors internal or external to patient 12. Upon receiving the signal, processor 204 adjusts at least one electrical stimulation therapy program of the plurality of electrical stimulation therapy programs. Examples of the one or more sensors include one or more sensors configured to measure a compound action potential of the patient 12, or a side effect indicative of a compound action potential. For example, the one or more sensors may be an accelerometer, a pressure sensor, a bending sensor, a sensor configured to detect a posture of patient 12, or a sensor configured to detect a respiratory function of patient 12. However, in other examples, external programmer 104 receives a signal indicating an evoked compound action potential in the target tissue of patient 12 and transmits the signal to processor 210. Processor 210 receives the signal via telemetry module 208.

As described above, in response to sensing an evoked compound action potential in the target tissue site of patient 12, or in response to receiving a signal indicative of the compound action potential, processor 210 adjusts at least one electrical stimulation therapy program of the plurality of electrical stimulation therapy programs. For example, processor 210 identifies a value for the one or more parameters defining the electrical stimulation therapy such that delivery of the electrical stimulation therapy does not evoke a compound action potential in the patient, e.g., by titration of the one or more parameters. In another example, processor 210 halts delivery of the electrical stimulation therapy according to the electrical stimulation therapy programs. In yet another example, processor 210 selects a different electrical stimulation therapy program of a plurality of electrical stimulation therapy programs that describe delivery of electrical stimulation therapy to patient 12. In yet another example, if a compound action potential is not evoked, processor 210 may increase amplitude of therapy until the action potential is evoked; however, processor 210 may increase amplitude of pulses that are delivered less frequently, resulting in little to no discomfort in the patient even if the action potential is evoked.

In some examples, a clinician uses external programmer 104 to transmit commands to processor 210 instructing processor 210 to perform titration of the one or more parameters describing the plurality of electrical stimulation therapy programs so as to calibrate the electrical stimulation therapy delivered by processor 210. For example, a clinician may perform such a titration to configure IMD 102 for delivery of therapy in an outpatient or post-implantation setting. In another example, during subsequent use by patient 12, processor 210, via electrodes 116, 118, periodically monitors the target tissue site of patient 12 for an evoked compound action potential. In response to sensing an evoked compound action potential, processor 210 adjusts the plurality of electrical stimulation therapy programs. Such an evoked compound action potential may arise over time due to impedance changes in leads 16 or electrodes 116, 118 of IMD 102, movement of the leads 16, or changes in the position of IMD 102 or leads 16. Processor 210 may determine that the occurrence of such an evoked action potential indicate a need to recalibrate one or more parameters of the electrical stimulation therapy delivered by processor 210. Alternatively, processor 210 may receive a signal indicating the occurrence of such an action potential from one or more sensors, as described above.

Upon detecting an evoked compound action potential, or upon receiving a signal indicative of the compound action potential from one or more sensors or external programmer 104, processor 210 suspends delivery of the electrical stimulation therapy to suppress the compound action potential, e.g., by suspending delivery of the electrical stimulation therapy for a predetermined amount of time. In one example, after suspending delivery of the electrical stimulation therapy for the predetermined amount of time, processor 210 resumes delivery of the electrical stimulation therapy. In another example, after the predetermined amount of time, processor 210 controls stimulation generator 202 to deliver electrical stimulation at a reduced amplitude. Processor 210, via electrodes 116, 118, senses an electrical parameter of the target tissue site of patient 12. Upon determining that the target tissue site continues to exhibit a compound action potential, processor 210 suspends delivery of the electrical stimulation for the predetermined amount of time.

In response to determining that an evoked compound action potential occurs, processor 210 suspends delivery of the electrical stimulation therapy to stop the compound action potential. In one example, after suspending delivery of the electrical stimulation therapy for a predetermined amount of time, processor 210 controls stimulation generator 202 to resume delivery of the electrical stimulation therapy. For example, evoked action potentials in patient 112 may result in significant but transient side effects, such as paresthesia, respiratory distress (i.e., coughing), or falling. Instead of attempting to determine a new amplitude for the electrical stimulation while the transient side effects are occurring, processor 210 suspends therapy to allow the transient side effects to dissipate and resumes therapy after the transient side effects have subsided. In some examples, if after several attempts to resume delivery of electrical stimulation fail (i.e., because compound action potentials are detected or because the side effects are still present), processor 210 may determine that the side effects are a new steady state for patient 112 given the present amplitude of electrical stimulation therapy. Accordingly, processor 210 may control stimulation generator 202 to perform titration, as described below, of one or more parameters describing the electrical stimulation therapy to determine an electrical stimulation that, when delivered according to a new set of electrical stimulation parameters, does not evoke an action potential in the tissue of patient 112.

In another example, after the predetermined amount of time, processor 210 controls stimulation generator 202 to deliver electrical stimulation therapy according to one or more reduced parameters, such as a reduced amplitude. Processor 210 senses, via electrodes of leads 16, an electrical parameter of the target tissue site of patient 12 to determine whether the electrical stimulation therapy according to the one or more reduced parameters continues to evoke a compound action potential. Upon determining that the target tissue site no longer exhibits a compound action potential, processor 210 controls stimulation generator 202 to resume delivery of the electrical stimulation therapy according to the one or more reduced parameters. Upon determining that the target tissue site continues to exhibit a compound action potential, processor 210 controls stimulation generator 202 to suspend the electrical stimulation therapy for another unit of the predetermined amount of time. Typically, the predetermined amount of time is in the order of minutes, e.g., approximately 1 minute, approximately 10 minutes, approximately 30 minutes, etc.

After the predetermined amount of time, processor 210 controls stimulation generator 202 to deliver electrical stimulation according to one or more parameters having further reduced magnitudes. Again, processor 210 determines whether the electrical stimulation according to one or more parameters having further reduced magnitudes continues to evoke a compound action potential. Upon determining that no such compound action potential is evoked, processor 210 gradually increases the magnitude of the one or more parameters and controls stimulation generator 202 to deliver electrical stimulation according to the gradually increasing one or more parameters. Processor 210 determines a point at which the electrical stimulation evokes a compound action potential to determine a threshold at which the magnitude of the one or more parameters defining the electrical stimulation therapy evokes a compound action potential. At this point, processor 210 reduces the magnitude of the one or more parameters by a percentage or ratio substantially below the magnitude of the one or more parameters that evokes a compound action potential. For example, the percentage or value may be 95%, 90%, 80%, or 60% of the magnitude of the one or more parameters that evoked the compound action potential, etc. Processor 210 controls stimulation generator 202 to deliver electrical stimulation therapy according to one or more parameters substantially below the threshold that evokes a compound action potential in the patient.

In other examples, upon detecting an evoked compound action potential, processor 210 automatically performs titration of one or more parameters defining the electrical stimulation therapy delivered to the patient to adjust the electrical stimulation therapy such that the electrical stimulation provides adequate therapy to the patient while remaining below a threshold that evokes a compound action potential in the tissue of the patient. In other words, upon detecting the evoked compound action potential, processor 210 automatically titrates one or more parameters defining the plurality of electrical stimulation therapy programs, for example, a voltage amplitude (for voltage controlled devices), a current amplitude (for current-controlled devices), a pulse width, or a pulse frequency, to gradually reduce the magnitude of the one or more parameters defining the plurality of electrical stimulation therapy programs. Upon determining a value for the one or more parameters defining the electrical stimulation therapy that does not evoke a compound action potential in patient 12, processor 210 selects that value for the one or more parameters and resumes delivery of the electrical stimulation therapy according to the new parameter set.

In some examples, processor 210 instructs stimulation generator 202 to deliver stimulation therapy that includes a first set of plurality of pulses having a first amplitude, and a second set of plurality of pulses having a second amplitude greater than the first amplitude. The one or more pulses of the second set of plurality of pulses are intermingled with sequential groups of pulses of the first set of plurality of pulses. Stimulation generator 202 may be configured to repeat alternate delivery of the groups of pulses of the first set of plurality of pulses for respective periods of time (e.g., a period of time is amount of time to deliver 200 pulses) and the one or more pulses of the second set of plurality of pulses at least until adjustment of the second amplitude is needed. In some examples, the respective periods of time for each group of pulses of the first set of plurality of pulses is the same (e.g., each group of pulses includes 200 pulses of the first set of plurality of pulses).

Because the second amplitude is greater than the first amplitude, pulses having the second amplitude may evoke an action potential. Also, because pulses having the second amplitude are delivered relatively infrequently, the evoking of the action potential may not cause the patient discomfort as compared to if the pulses having the first amplitude, which are delivered more frequently, evoke the action potential.

There may be various triggers for adjusting the second amplitude. As one example, every time an action potential is evoked, processor 210 may adjust the amplitude level of the second amplitude. However, because pulses having the second amplitude may not cause discomfort even if an action potential is evoked, it may not be necessary to adjust the amplitude every time an action potential is evoked. Other examples of triggers to adjust the second amplitude include lead migration, changes in impedance of electrodes 116, 118, a periodic trigger to adjust therapy, a random trigger to adjust therapy, and change in patient motion or posture, as a few non-limiting examples.

Processor 210 may adjust the second amplitude to an adjusted second amplitude until the adjusted amplitude is less than or equal to an activation threshold (e.g., a threshold where an action potential is evoked) based on the second amplitude being greater than the activation threshold. For example, processor 210 may determine whether the action potential is invoked, such as after delivery of pulses having the second amplitude, based on techniques to determine whether the action potential is invoked described in this disclosure. Processor 210 may adjust the second amplitude downwards until determined that the action potential is not evoked. In some cases, by adjusting the second amplitude downwards, processor 210 may undershoot the second amplitude so that the adjusted second amplitude is less than the activation threshold. Processor 210 increase the adjusted second amplitude, to compensate for the undershooting, until the adjusted second amplitude is substantially equal to the activation threshold (e.g., within ±5 to 10% of the activation threshold).

In some cases, the amplitude from the pulses having the second amplitude may not evoke an action potential. In such cases, the therapy may not be as effective as possible. Processor 210 may adjust the second amplitude to the adjusted second amplitude until the adjusted second amplitude is greater than or equal to the activation threshold based on the second amplitude being less than the activation threshold (e.g., pulses having the second amplitude are not evoking an action potential). For example, processor 210 may determine whether the action potential is invoked, such as after delivery of pulses having the second amplitude, based on techniques to determine whether the action potential is invoked described in this disclosure. Processor 210 may adjust the second amplitude upwards until determined that the action potential is evoked. In some cases, by adjusting the second amplitude upwards, processor 210 may overshoot the second amplitude so that it is greater than the activation threshold. Processor 210 reduce the adjusted second amplitude, to compensate for the overshooting, until the adjusted second amplitude is substantially equal to the activation threshold (e.g., within ±5 to 10% of the activation threshold).

Processor 210 may adjust the first amplitude based on the adjusted second amplitude. For example, the adjusted second amplitude may be a little bit greater than, equal to, or a little bit less than the activation threshold (e.g., within a range of ±20% of the activation threshold). Processor 210 may adjust the first amplitude such that the adjusted second amplitude is a defined level below the adjusted second amplitude. The first adjusted amplitude may be 80% of the second adjusted amplitude, as one example. In this way, the first adjusted amplitude is very highly likely to be below the activation threshold, and delivery of pulses having the first adjusted amplitude at a high frequency may not cause patient discomfort.

Processor 210 may then cause stimulation generator 202 to deliver stimulation therapy based at least on the adjusted first amplitude. For example, processor 210 may then cause stimulation generator 202 to deliver stimulation therapy that includes a third set of plurality of pulses having the adjusted first amplitude, and a fourth set of plurality of pulses having the adjusted second amplitude. One or more pulses of the fourth set of plurality of pulses having the adjusted second amplitude may be intermingled with groups of pulses of the third set of plurality of pulses having the first adjusted amplitude. Stimulation generator 202 may keep delivering these pulses until another adjustment trigger.

In some examples, stimulation generator 202 may deliver the third set of plurality of pulses and the fourth set of plurality of pulses using the same ones of electrodes 116, 118. In other examples, stimulation generator 202 may deliver the third set of plurality of pulses with a first set of electrodes 116, 118 on leads 16A, 16B to deliver relatively high frequency therapy (e.g., because the third set of plurality of pulses are delivered relatively frequently), and deliver the fourth set of plurality of pulses with a second set of electrodes 116, 118 on leads 16A, 16B to deliver relatively low frequency stimulation therapy (e.g., because the fourth set of plurality of pulses are delivered relatively infrequently).

For therapy delivery, the pulse widths of the pulses having the first and second amplitudes, and the pulse widths of the pulses having the adjusted first and second amplitudes may be the same. In some examples, the pulse widths of the pulses having the first and second amplitudes, and the pulse widths of the pulses having the adjusted first and second amplitudes may be different. Also, the pulse widths of pulses having the second adjusted amplitude may be different than the pulse widths of pulses having the first adjusted amplitude. Similarly, the pulse widths of pulses having the second amplitude may be different than the pulse widths of pulses having the first amplitude.

Although IMD 102 is generally described herein as an implantable device, the techniques of this disclosure may also be applicable to external or partially external medical devices in other examples. For example, IMD 102 may instead be configured as an external medical device coupled to one or more percutaneous medical leads. The external medical device may be a chronic, temporary, or trial electrical stimulator. In addition, an external electrical stimulator may be used in addition to one or more IMDs 102 to deliver electrical stimulation as described herein.

Figure 3:
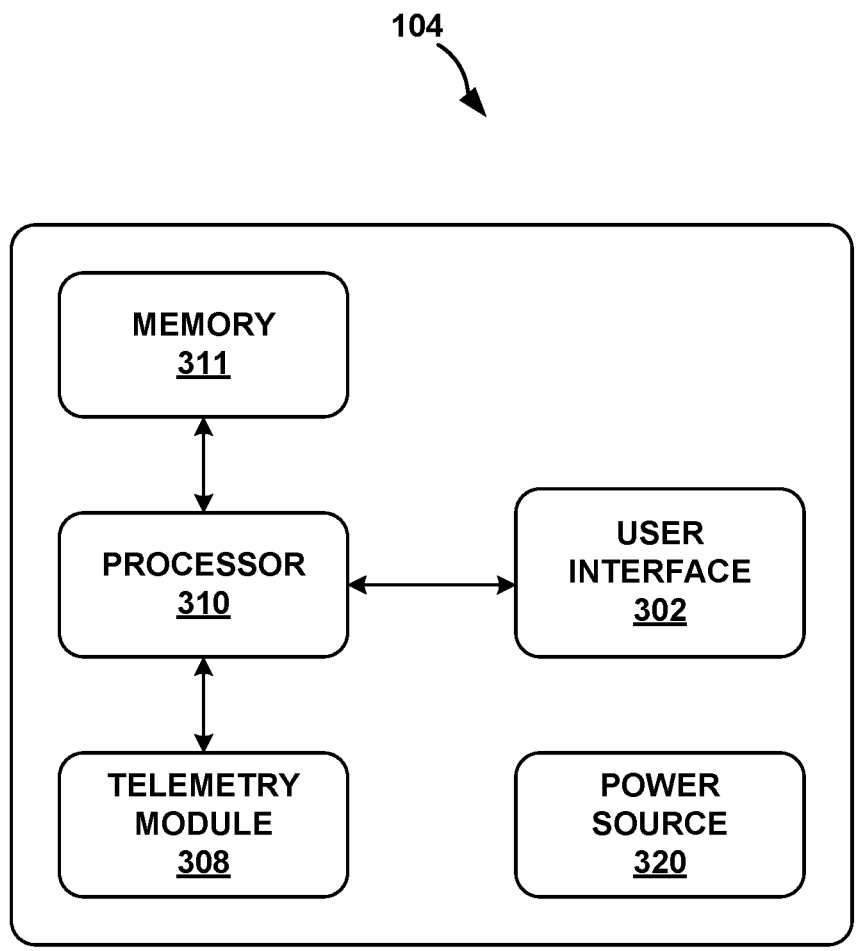
FIG. 3 is a block diagram of the example external programmer of FIG. 1.

FIG. 3 is a block diagram of the example external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, such as one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 are functionally integrated. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, or receive a user input and send a corresponding command to IMD 102, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Processor 310 may also control user interface 302 to display information related to an anatomical atlas (e.g., an atlas of a reference anatomy) and patient-specific anatomy. For example, user interface 302 may display a representation of one or more atlas-defined anatomical structures over a representation (e.g., an image) of the specific patient anatomy. User interface 302 may present annotation tools for adjusting the structures of the atlas to the patient anatomy and receive user annotations indicating where the corresponding structures of the patient anatomy are located and/or where the atlas should be moved with respect to the patient anatomy. Processor 310 may then adjust the position and/or size of the structures of the atlas to more closely match (e.g., a best fit) to the user annotation. After the atlas has been adjusted, the user may refer to the atlas for locations of certain structures of the patient instead of needing to continually find desired structures based on the image of the patient anatomy.

Telemetry module 308 may support wireless communication between IMD 102 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna.

Examples of local wireless communication techniques that may be employed to facilitate communication between programmer 104 and IMD 102 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 102 for delivery of stimulation therapy.

In some examples, selection of therapy parameters or therapy programs may be transmitted to a medical device (e.g., IMD 102) for delivery to patient 12. In other examples, the therapy may include medication, activities, or other instructions that patient 12 must perform themselves or a caregiver perform for patient 12. In some examples, programmer 104 may provide visual, audible, and/or tactile notifications that indicate there are new instructions. Programmer 104 may require receiving user input acknowledging that the instructions have been completed in some examples.

According to the techniques of the disclosure, processor 310 of external programmer 104 receives, via user interface 302, input from a clinician causing processor 310, via telemetry module 308, to instruct IMD 102 to deliver electrical stimulation therapy according to one or more electrical stimulation therapy programs to a target tissue site of the spinal column 20 of patient 12 via a plurality of electrodes. In some examples, processor 310 of external programmer 104 receives, via user interface 302, input from a clinician causing processor 310, via telemetry module 308, to instruct IMD 102 to titrate one or more parameters defining the plurality of electrical stimulation therapy programs, for example, a voltage amplitude (for voltage controlled devices), a current amplitude (for current-controlled devices), a pulse width, or a pulse frequency, to deliver electrical stimulation of gradually increasing strength.

During delivery of electrical stimulation therapy according to the one or more electrical stimulation programs, IMD 102, via electrodes interposed along leads 16, senses the target tissue site of the spinal column 20 of patient 12 and measures the electrical activity of the target tissue site. In one example, processor 310 of external programmer 104 receives, via telemetry module 308, signals from IMD 102 indicating the measured electrical activity. Upon determining that the measured electrical activity indicates that electrical stimulation therapy according to the one or more electrical stimulation therapy programs evokes a compound action potential in the target tissue site of patient 12, processor 310, via telemetry module 308, instructs IMD 102 to adjust at least one electrical stimulation therapy program of the plurality of electrical stimulation therapy programs. In some examples, processor 310 accomplishes this by issuing, via telemetry module 308, a notification of the sensed evoked compound action potential to IMD 102.

In an alternative example, processor 310 receives, from one or more sensors internal or external to patient 12, a signal indicating that electrical stimulation therapy according to the one or more electrical stimulation programs evokes a compound action potential in the target tissue site of patient 12. Upon receiving the signal, processor 310, via telemetry module 308, instructs IMD 102 to adjust at least one electrical stimulation therapy program of the plurality of electrical stimulation therapy programs. Such an example signal may include a signal indicating an electrically-evoked compound action potential (eCAP) of the tissue of the patient. Other examples of the signal include a signal received from one or more sensors configured to measure a compound action potential of the patient 12, or a side effect indicative of a compound action potential. For example, the signal may be a signal received from an accelerometer, a pressure sensor, a bending sensor, a sensor configured to detect a posture of patient 12, or a sensor configured to detect a respiratory function of patient 12.

As described above, in response to determining that a compound action potential in the target tissue site of patient 12 is present, processor 310, via telemetry module 308, instructs IMD 102 to adjust at least one electrical stimulation therapy program of the plurality of electrical stimulation therapy programs. For example, processor 310 selects different values for the one or more parameters defining the electrical stimulation therapy such that delivery of the electrical stimulation therapy does not evoke a compound action potential in the patient, and instructs, via telemetry module 308, IMD 102 to deliver electrical stimulation therapy according to the selected one or more parameters defining the electrical stimulation therapy. In another example, processor 310, via telemetry module 308, instructs IMD 102 to halt delivery of the electrical stimulation therapy. In yet another example, processor 310 selects a different electrical stimulation therapy program of the plurality of electrical stimulation therapy programs and instructs, via telemetry module 308, IMD 102 to deliver electrical stimulation therapy according to the selected electrical stimulation therapy program.

In some examples, processor 310 of external programmer 104 receives, via user interface 302, input from a user causing processor 310, via telemetry module 308, to transmit commands to IMD 102 instructing IMD 102 to perform titration of the one or more parameters describing the plurality of electrical stimulation therapy programs so as to calibrate the electrical stimulation therapy. For example, a clinician may perform such a titration to configure system 100 for delivery of therapy in an outpatient or post-implantation setting. In another example, In this example, patient 12, via external programmer 104, performs such a titration to reconfigure IMD 102 such that emergent side effects are reduced or suppressed. In yet another example, during subsequent use by patient 12, processor 310, via telemetry module 308, receives signals from IMD 102 or one or more sensors indicating a physiological parameter of a tissue area of patient 12. Processor 310 may determine that such signals indicate the presence of an evoked compound action potential, and thus indicate a need to recalibrate one or more parameters of the electrical stimulation therapy delivered by IMD 102.

Upon determining that the physiological parameter is indicative of an evoked compound action potential, processor 310, via telemetry module 308, transmits instructions to IMD 102 to adjust the one or more electrical stimulation therapy programs describing the electrical stimulation therapy, suspend delivery of the electrical stimulation, or perform titration of one or more parameters defining the electrical stimulation therapy as described above.

Figure 4:
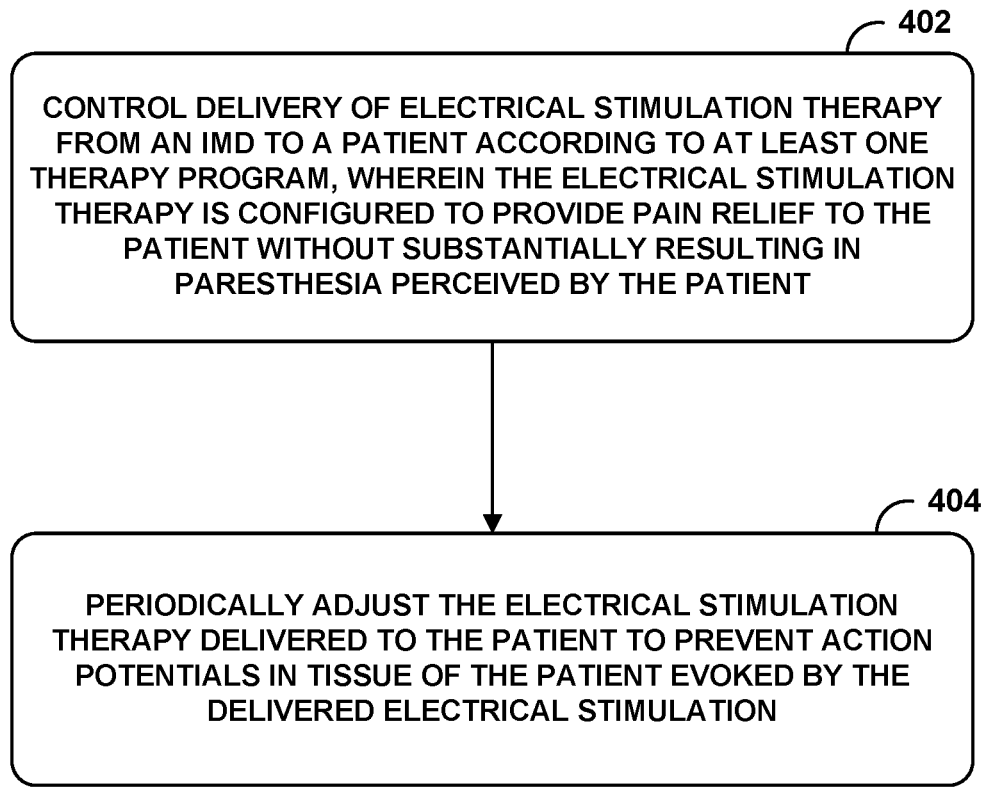
FIG. 4 is a flowchart illustrating an example operation for delivering SCS therapy according to the techniques of the disclosure.

FIG. 4 is a flowchart illustrating an example operation for delivering SCS therapy according to the techniques of the disclosure. For ease of description, FIG. 4 is described with respect to system 100 shown in FIGS. 1 to 3.

As depicted in FIG. 4, processor 210 controls stimulation generator 202 to deliver electrical stimulation therapy to a target tissue site of the spinal column 20 of patient 12 via electrodes 116, 118 interposed along leads 16. Processor 210 may control the delivery of electrical stimulation therapy according to one or more electrical stimulation therapy programs defining the therapy. In some examples, the electrical stimulation therapy programs are configured to provide pain relief to patient 12 without substantially inducing paresthesia or other side effects in patient 12.

During delivery of electrical stimulation therapy to patient 12 according to the one or more electrical stimulation programs (402), processor 210 periodically adjusts the electrical stimulation therapy delivered to the patient to prevent action potentials in the tissue of the patient evoked by the delivered electrical stimulation (404). For example, over time, the delivered stimulation may evoke compound action potentials, e.g., for the reasons described above, even though the therapy did not initially evoke compound action potentials when a clinician initially configured the electrical stimulation system. In some examples, processor 210 determines when the delivered electrical stimulation 402 evokes a compound action potential and adjusts the stimulation therapy in response to the determination (404). As described herein, the adjusted therapy does not result in an evoked compound action potential in the tissue during subsequent delivery of the electrical stimulation therapy.

For example, IMD 102, via the electrodes 116, 118 interposed on leads 16, senses target tissue site of the spinal column 20 of patient 12 to measure the electrical activity of the target tissue site. Processor 210 determines that the delivered electrical stimulation therapy evokes a compound action potential in the target tissue site of patient 12, and in response, adjusts the electrical stimulation therapy as described above. Processor 210 may determine that the compound action potentials are evoked by sensing the compound action potential via electrodes 116, 118, or other sensing device. In other examples, processor 210 may receive patient input indicating that the patient is experiencing paresthesia. In response to the receipt of the patient input, processor 210 may adjust the electrical stimulation therapy. In some examples, processor 210 adjusts the electrical stimulation therapy periodically based on the amount of time since the last adjustment, e.g., on a daily or weekly basis. In some example, processor 210 may initiate the adjustment to the therapy based on patient activity. For example, processor 210 may determine the patient has transitioned from a prone position to a sitting position, from a prone position to a supine position, from a sitting position to a running position, etc.

In some examples, the one or more sensors are internal or external to patient 12. Such an example signal may include a signal indicating an electrically-evoked compound action potential (eCAP) of the tissue of the patient. Other examples of the signal include a signal received from one or more sensors configured to measure a compound action potential of the patient 12, or a side effect indicative of a compound action potential. For example, IMD may receive a signal from an accelerometer, a pressure sensor, a bending sensor, a sensor configured to detect a posture of patient 12, or a sensor configured to detect a respiratory function of patient 12. Such a sensor, for example, may be configured to detect when patient 112 is running, walking, standing, sitting, laying down, prone, supine, and the like (e.g., for a posture sensor), or coughing or suffering respiratory distress in patient 12 (e.g., for a sensor configured to detect respiratory function). However, in other examples, external programmer 104 receives a signal indicating a compound action potential in the target tissue of patient 12 and transmits a notification of a sensed evoked compound action potential to IMD 102.

In response to sensing the evoked compound action potential, IMD 102 adjusts at least one electrical stimulation therapy program of the plurality of electrical stimulation therapy programs (404). In one example, IMD 102 selects a value for the one or more parameters defining the electrical stimulation therapy such that delivery of the electrical stimulation therapy does not evoke a compound action potential in the patient. As another example, IMD 102 halts delivery of the electrical stimulation therapy. In yet another example, IMD 102 selects a different electrical stimulation therapy program of the plurality of electrical stimulation therapy programs describing the delivery of electrical stimulation to patient 12.

Figure 5:
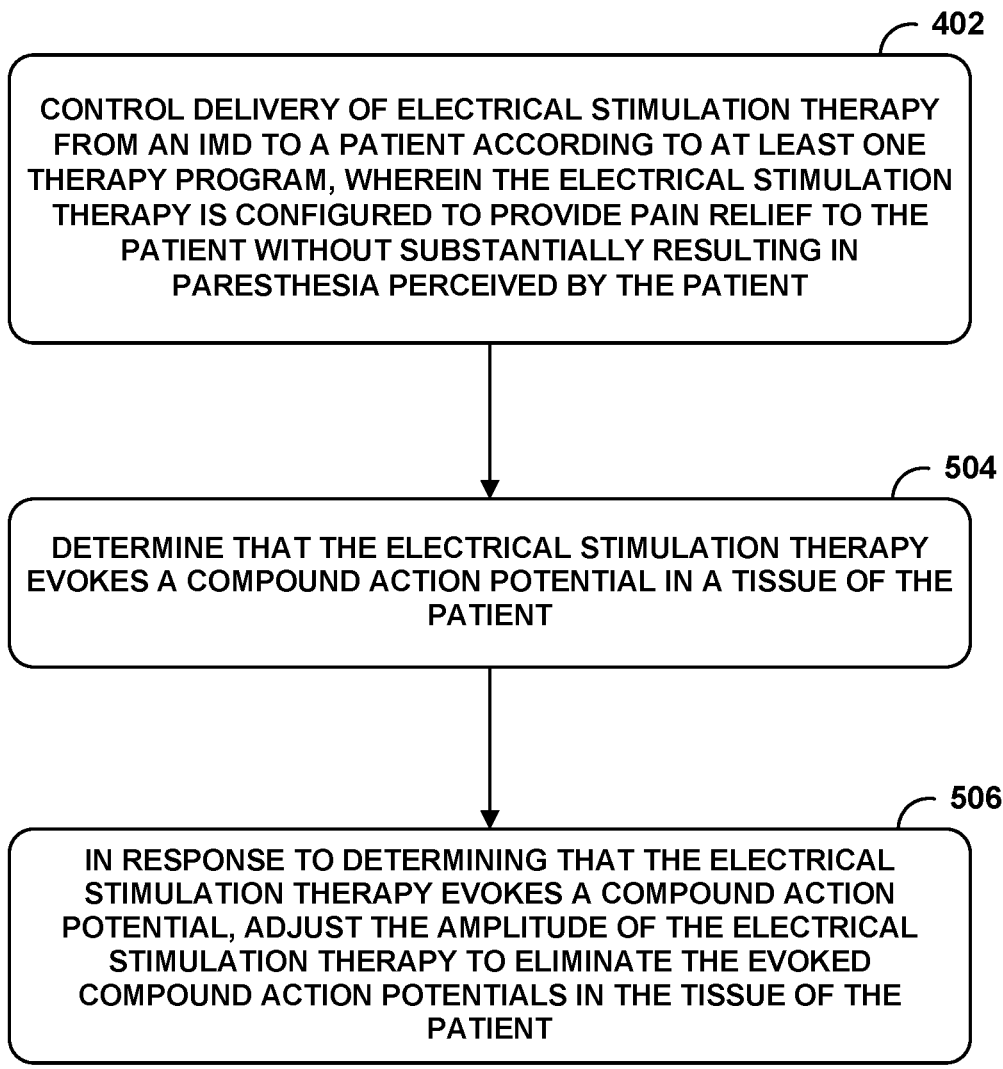
FIG. 5 is a flowchart illustrating an example operation for delivering SCS therapy according to the techniques of the disclosure.

FIG. 5 is a flowchart illustrating an example operation for delivering SCS therapy according to the techniques of the disclosure. For convenience, FIG. 5 is described with respect to system 100 of FIGS. 1 to 32.

As depicted in FIG. 5, processor 210 controls stimulation generator 202 to deliver electrical stimulation therapy according to one or more electrical stimulation therapy programs to a target tissue site of the spinal column 20 of patient 12 via electrodes 116, 118 interposed along leads 16 (402), e.g. as described with regard to FIG. 4.

During delivery of electrical stimulation therapy to patient 12 according to the one or more electrical stimulation programs (402), processor 210 controls delivery of electrical stimulation therapy from IMD 102 to patient 112 according to at least one therapy program. In some examples, the electrical stimulation therapy is configured to provide pain relief to the patient without substantially resulting in paresthesia perceived by the patient. In other examples, the electrical stimulation therapy is configured to provide pain relief to the patient while causing no paresthesia perceived by the patient.

Processor 210 determines that the electrical stimulation therapy evokes a compound action potential in the target tissue of patient 112 (504). For example, over time, the delivered stimulation may evoke compound action potentials, e.g., for the reasons described above, even though the therapy did not initially evoke compound action potentials when a clinician initially configured the electrical stimulation system. In some examples, processor 210 senses, via the electrodes 116, 118 interposed on leads 16, target tissue site of the spinal column 20 of patient 12 to measure the electrical activity of the target tissue site. In some examples, processor 210 senses an electrically-evoked compound action potential (eCAP) of the tissue of patient 112. In an alternative example, processor 210 determines that the electrical stimulation therapy is evoking a compound action potential by monitoring, via one or more sensors, one or more physiological parameters of patient 12 (e.g., to determine if the patient is suffering from one or more side effects caused by evoked action potentials, such as coughing or falling). In some examples, the one or more sensors are internal or external to patient 12. For example, the sensor may be an accelerometer, a pressure sensor, a bending sensor, a sensor configured to detect a posture of patient 12, or a sensor configured to detect a respiratory function of patient 12. In yet a further example, processor 210 determines that the electrical stimulation therapy is evoking a compound action potential by sensing, via the electrodes 116, 118 interposed on leads 16, target tissue site of the spinal column 20 of patient 12 to measure electrical activity of the target tissue site and by monitoring, via one or more sensors, one or more physiological parameters of patient 12. In a still further example, processor 210 determines that the electrical stimulation therapy is evoking a compound action potential based on receiving feedback from patient 112 indicating that the patient 112 is experiencing side effects, such as paresthesia, due to evoked action potentials.

In response to determining that the electrical stimulation therapy evokes a compound action potential, processor 210 adjusts one or more parameters defining the stimulation therapy to eliminate the evoked compound action potentials in the tissue of the patient (506). As described herein, the adjusted therapy does evoke compound action potential in the tissue during subsequent delivery of the electrical stimulation therapy. In some examples, processor 210 reduces the magnitude of the one or more parameters defining the electrical stimulation therapy program (e.g., a current amplitude, a voltage amplitude, a frequency, a pulse width, etc). In one example, processor 210 selects a value for the one or more parameters defining the electrical stimulation therapy such that delivery of the electrical stimulation therapy does not evoke a compound action potential in the patient. In the example of a voltage-controlled system where IMD 102 gradually increases the voltage amplitude of the plurality of electrical stimulation therapy programs, upon detecting an evoked compound action potential, IMD 102 determines that the voltage amplitude is at a magnitude that evokes a compound action potential in patient 12. Accordingly, IMD 102 selects a value for this voltage amplitude that is less than the voltage amplitude at the level that evokes the compound action potential in patient 12. In the example of a current-controlled system where IMD 102 gradually increases the current amplitude of the plurality of electrical stimulation therapy programs, upon detecting an evoked compound action potential, IMD 102 determines that the current amplitude is at a magnitude that evokes a compound action potential in patient 12. Accordingly, IMD 102 selects a value for the current amplitude that is less than the current amplitude at the level that evokes the compound action potential in patient 12. Thus, IMD 102 continues to deliver electrical stimulation therapy at the new value for the one or more parameters defining the plurality of electrical stimulation therapy programs at a level that does not evoke a compound action potential in patient 12, thereby decreasing the severity of side effects experienced by patient 12.

In some examples, the operation depicted in FIG. 5 is performed by a clinician to configured electrical stimulation therapy delivered by IMD 102 in an out-patient or post-implantation setting. In other examples, the operation depicted in FIG. 5 is performed by patient 12 to recalibrate the electrical stimulation therapy delivered by IMD 102. For example, patient 12 may experience side effects caused by an evoked compound action potential, and, via external programmer 104, instruct IMD 104 to recalibrate the electrical stimulation therapy such that the electrical stimulation therapy does not evoke a compound action potential in patient 12. In still further examples, IMD 104 may automatically perform the operation depicted in FIG. 5 to periodically recalibrate the electrical stimulation therapy such that the electrical stimulation therapy does not evoke a compound action potential in patient 12. Such periodic recalibration may occur on a weekly, monthly, or yearly basis, for example.

Figure 6:
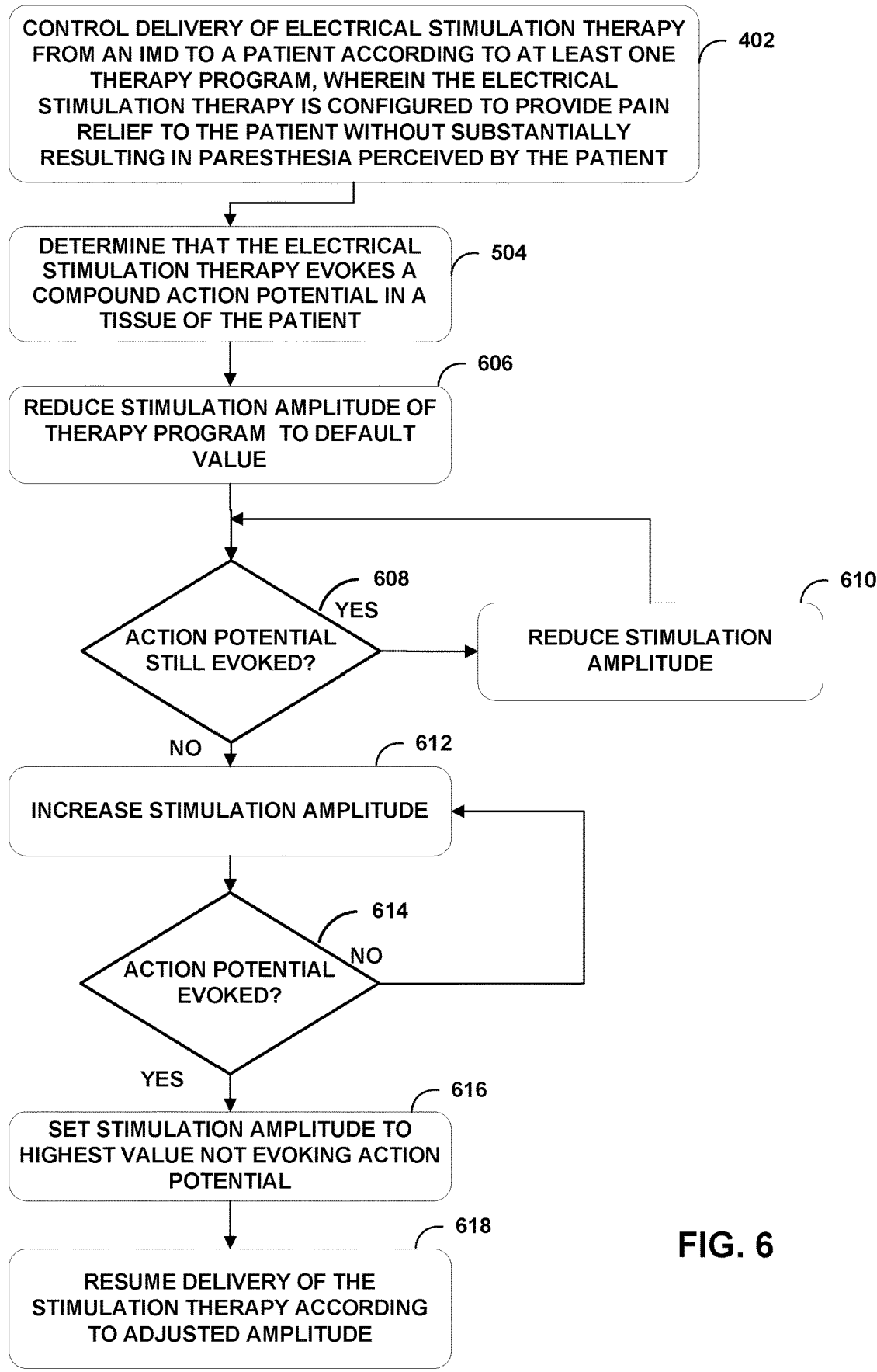
FIG. 6 is a flowchart illustrating an example operation for delivering SCS therapy according to the techniques of the disclosure.

FIG. 6 is a flowchart illustrating an example operation for delivering SCS therapy according to the techniques of the disclosure. For convenience, FIG. 6 is described with respect to system 100 of FIGS. 1 to 3.

As depicted in FIG. 6, processor 210 controls stimulation generator 202 to deliver electrical stimulation therapy according to one or more electrical stimulation therapy programs to a target tissue site of the spinal column 20 of patient 12 via electrodes 116, 118 interposed along leads 16 (402), e.g. as described with regard to FIG. 4. During delivery of electrical stimulation therapy to patient 12 according to the one or more electrical stimulation programs (402), processor 210 determines when the delivered electrical stimulation 402 evokes a compound action potential and adjusts the stimulation therapy in response to the determination (504), e.g., as described with regard to FIG. 5.

In response to detecting an evoked compound action potential, IMD 102 reduces the magnitude of the amplitude of the electrical stimulation therapy program to a default or preprogrammed magnitude and resumes delivery of electrical stimulation therapy (606). For example, IMD 102 may reduce the amplitude by 5%, 10%, or 20% of its previous value (e.g., such that the amplitude is 95%, 90%, 80% of its previous magnitude). In other examples, IMD 102 may reduce the amplitude by a predetermined amount. In still further examples, IMD 102 may reduce one or more parameters in addition to, or as an alternative to, reducing the amplitude. For example, for a current-controlled system, IMD 102 reduces the current amplitude to a default or preprogrammed magnitude. Similarly, in an example of a voltage-controlled system, IMD 102 reduces the voltage amplitude to a default magnitude. In some examples, prior to resuming the delivery of the electrical stimulation therapy at the reduced amplitude, IMD 102 waits for a predetermined amount of time, and during this time, IMD 102 does not deliver therapy to patient 12. Typically, the predetermined amount of time is in the order of minutes, e.g., approximately 1 minute, approximately 10 minutes, approximately 30 minutes, etc.

IMD 102, via one or more sensors, determines whether electrical stimulation therapy according to an electrical stimulation therapy program at the default magnitude, still evokes a compound action potential in the tissue of patient 12 (608). In some examples, processor 210 of IMD 102 controls delivery electrical stimulation therapy according to the reduced amplitude for a limited duration, such as by delivering a single pulse of the electrical stimulation. In another example, IMD 102, via electrodes 116, 118, determines whether the electrical stimulation causes an electrical parameter of the target tissue site of patient 12 to be greater than a predetermined threshold correlated to a likelihood of evoking compound action potentials in the tissue site of patient 12. In other words, IMD 102 may sense an electrical parameter of the target tissue site of patient 112, such as one of a voltage or a current. IMD 102 may determine whether the electrical parameter is greater than the predetermined threshold. In some examples, the predetermined threshold is a magnitude of the electrical parameter a value that is slightly less than the electrical energy required to evoke a compound action potential in the target tissue of patient 12 (e.g., 5% less, 10% less, 20% less, etc.).

If IMD 102 determines that the electrical stimulation evokes a compound action potential (e.g., "YES" block of 608), IMD 102 further reduces the magnitude of the electrical stimulation therapy program and returns to step 608. For example, if IMD 102 determines that electrical stimulation therapy according to an amplitude that is 80% of a previous maximum amplitude evokes a compound action potential, IMD 102 may deliver electrical stimulation therapy according to an amplitude that is 60% of a previous maximum amplitude and determine whether this electrical stimulation therapy evokes a compound action potential. This cycle is repeated until IMD 102 determines that the magnitude of the electrical stimulation therapy program does not evoke a compound action potential in the tissue of patient 12 (e.g. "NO" block of 608). For example, if IMD determines that electrical stimulation therapy according to the amplitude that is 60% of the previous maximum amplitude still evokes a compound action potential, IMD 102 may deliver electrical stimulation therapy according to an amplitude that is 40% of the previous maximum amplitude and determine whether this electrical stimulation therapy evokes a compound action potential. While the example of FIG. 6 is described with respect to adjustment of the stimulation amplitude, in other examples, other stimulation parameters, such as pulse width or pulse frequency, may be adjusted.

At this point, IMD 102 slightly increases the magnitude of the electrical stimulation therapy program (612) and determines, via the one or more sensors, whether the electrical stimulation therapy program evokes a compound action potential in the tissue of patient 12 (614). As described above, in some examples, this gradual adjustment is an incremental or decremental adjustment, such as with a step function. In other examples, the gradual adjustment is continuous adjustment that is a substantially smooth increase or decrease in the value of the parameter. If the magnitude of the electrical stimulation therapy program does not evoke a compound action potential in the tissue of patient 12 (e.g. "NO" block of 614), then IMD returns to step 612 and slightly increases the magnitude of the electrical stimulation therapy program (612). This cycle continues until IMD 102 determines that the magnitude of the electrical stimulation therapy program does evoke a compound action potential in the tissue of patient 12 (e.g. "YES" block of 614).

By titrating the electrical stimulation therapy in the above-described manner, IMD 102 may determine the highest value for the one or more parameters defining the electrical stimulation therapy that does not evoke a compound action potential. For example, IMD 102 may determine a maximum or relatively large current amplitude (for a current-controlled system) or a maximum or relatively large voltage amplitude (for a voltage-controlled system) that does not evoke a compound action potential in the target tissue site of patient 12. Accordingly, IMD 102 selects a value for the one or more parameters defining the electrical stimulation therapy that does not evoke a compound action potential (616) and resumes delivery of the electrical stimulation therapy according to the highest value for the one or more parameters (618). As one example, IMD 102 may determine a new amplitude for the electrical stimulation therapy by applying a ratio (e.g., from 0.1 to 1.0) or a percentage (e.g., from 10% to 100%) to the previous amplitude of the electrical stimulation therapy to select an amplitude for the electrical stimulation therapy that is substantially below a threshold amplitude that evokes a compound action potential. In some examples, the ratio or percentage is a ratio or percentage of a first electrical stimulation amplitude that evoked a compound action potential. In other examples, the ratio or percentage is a ratio or percentage of a previous electrical stimulation amplitude that did not evoke a compound action potential. Generally, the ratio or percentage is different for each patient. In some examples, the patient provides feedback via external programmer 104 to adjust the value of the ratio or percentage to prevent sensations of paresthesia during subsequent electrical stimulation therapy as the electrical stimulation therapy changes over time.

Figure 7:
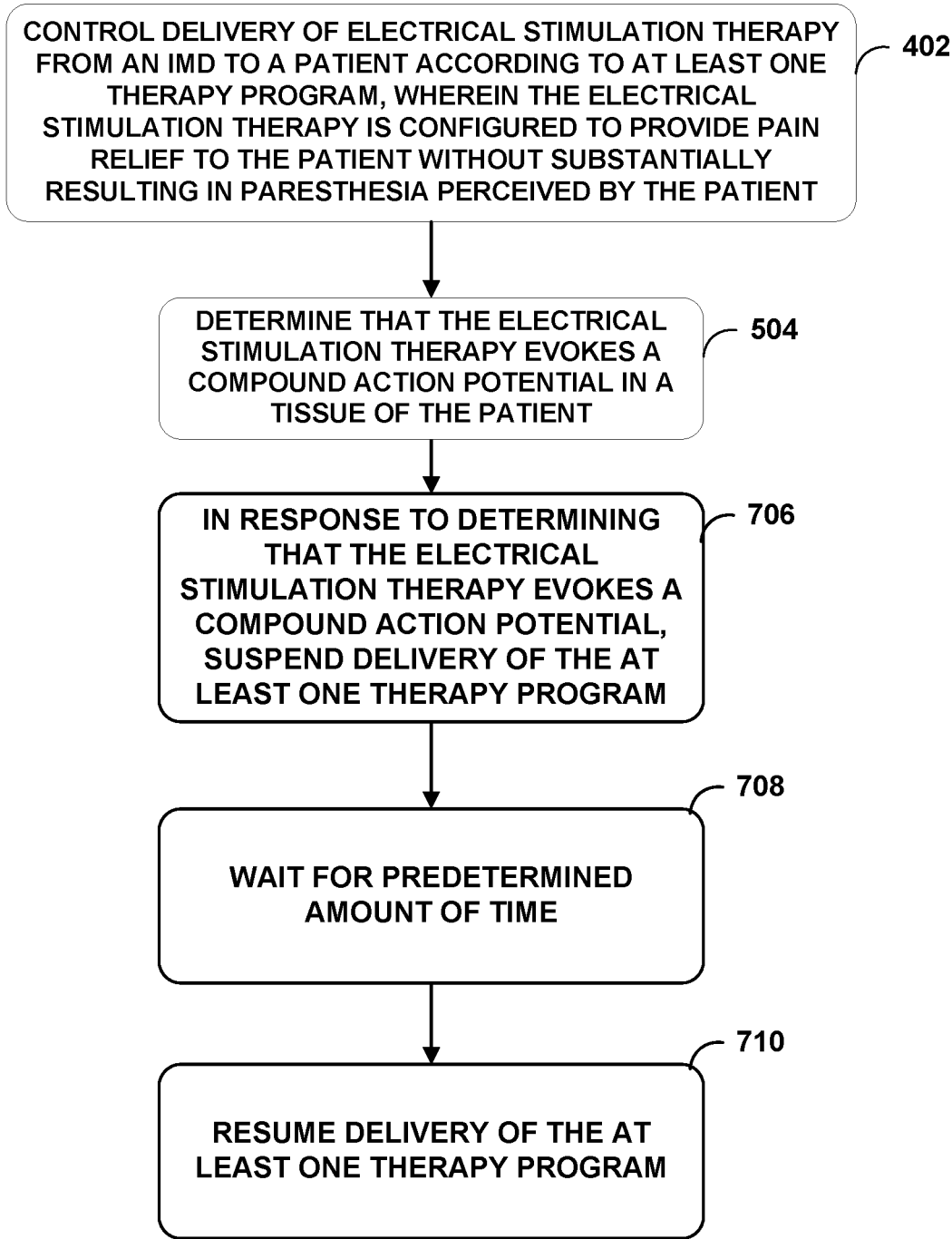
FIG. 7 is a flowchart illustrating an example operation for delivering SCS therapy according to the techniques of the disclosure.

FIG. 7 is a flowchart illustrating an example operation for delivering SCS therapy according to the techniques of the disclosure. For convenience, FIG. 7 is described with respect to FIGS. 1 and 2. The operations of FIG. 7 are substantially similar to the operations described above with respect to FIG. 6.

As depicted in FIG. 7, processor 210 controls stimulation generator 202 to deliver electrical stimulation therapy according to one or more electrical stimulation therapy programs to a target tissue site of the spinal column 20 of patient 12 via electrodes 116, 118 interposed along leads 16 (402), e.g. as described with regard to FIG. 4. During delivery of electrical stimulation therapy to patient 12 according to the one or more electrical stimulation programs (402), processor 210 determines when the delivered electrical stimulation 402 evokes a compound action potential and adjusts the stimulation therapy in response to the determination (504), e.g., as described with regard to FIG. 5.

In response to receiving a signal indicative of a compound action potential, IMD 102 suspends delivery of electrical stimulation therapy (706). IMD 102 waits for a predetermined amount of time, and during this time, IMD 102 does not deliver therapy to patient 12 (708). In some examples, the predetermined amount of time is in the order of seconds or minutes, e.g., approximately 1 second, approximately 10 seconds, approximately 30 seconds, approximately 1 minute, approximately 10 minutes, approximately 30 minutes, etc. After the predetermined amount of time has elapsed, IMD 102 resumes delivery of the electrical stimulation therapy (710). In some examples, IMD 102 resumes delivery of the electrical stimulation therapy according to the same electrical stimulation parameter set. In other examples, IMD 102 adjusts one or more parameters defining the electrical stimulation therapy, in a manner similar to that described above, prior to resuming delivery of the electrical stimulation therapy.

Figure 8:
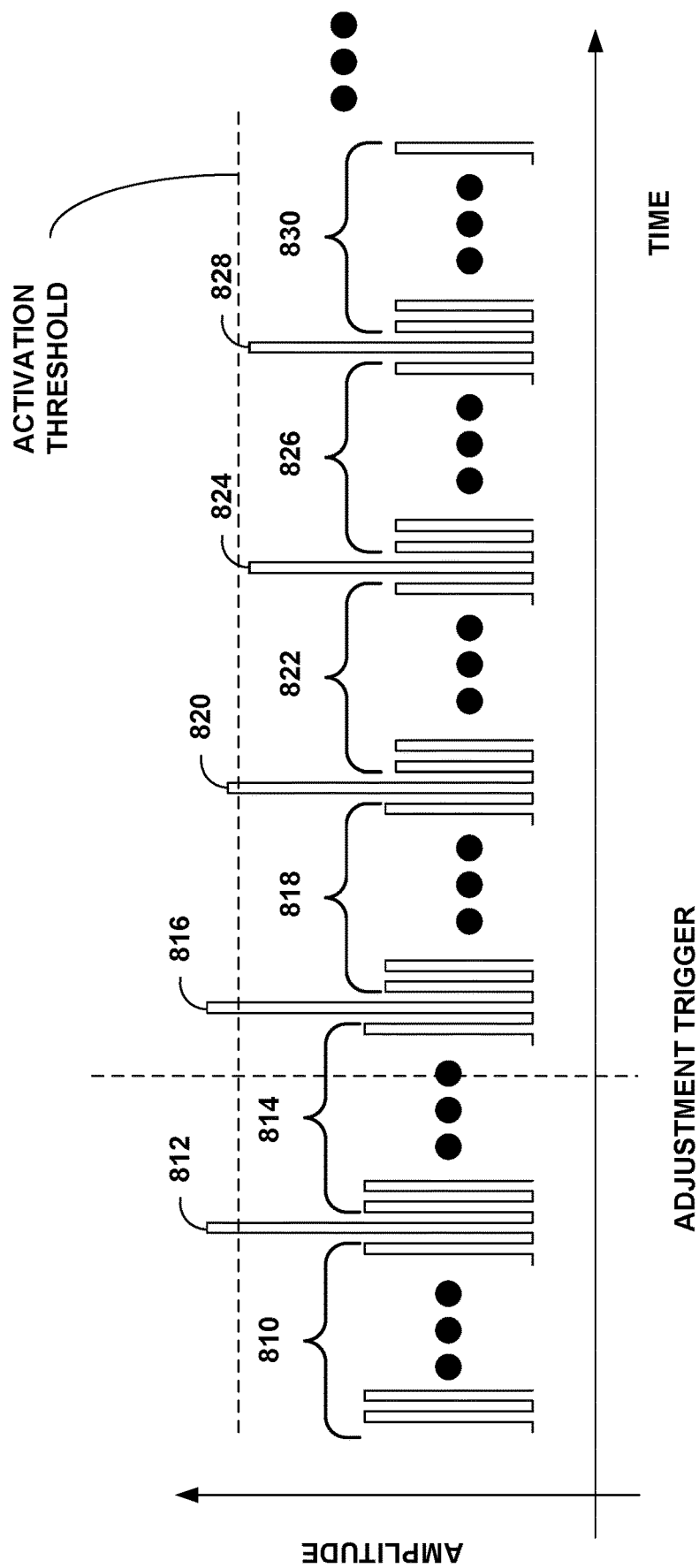
FIG. 8 is a timing diagram illustrating an example operation for delivering therapy according to the techniques of this disclosure.
Figure 9:
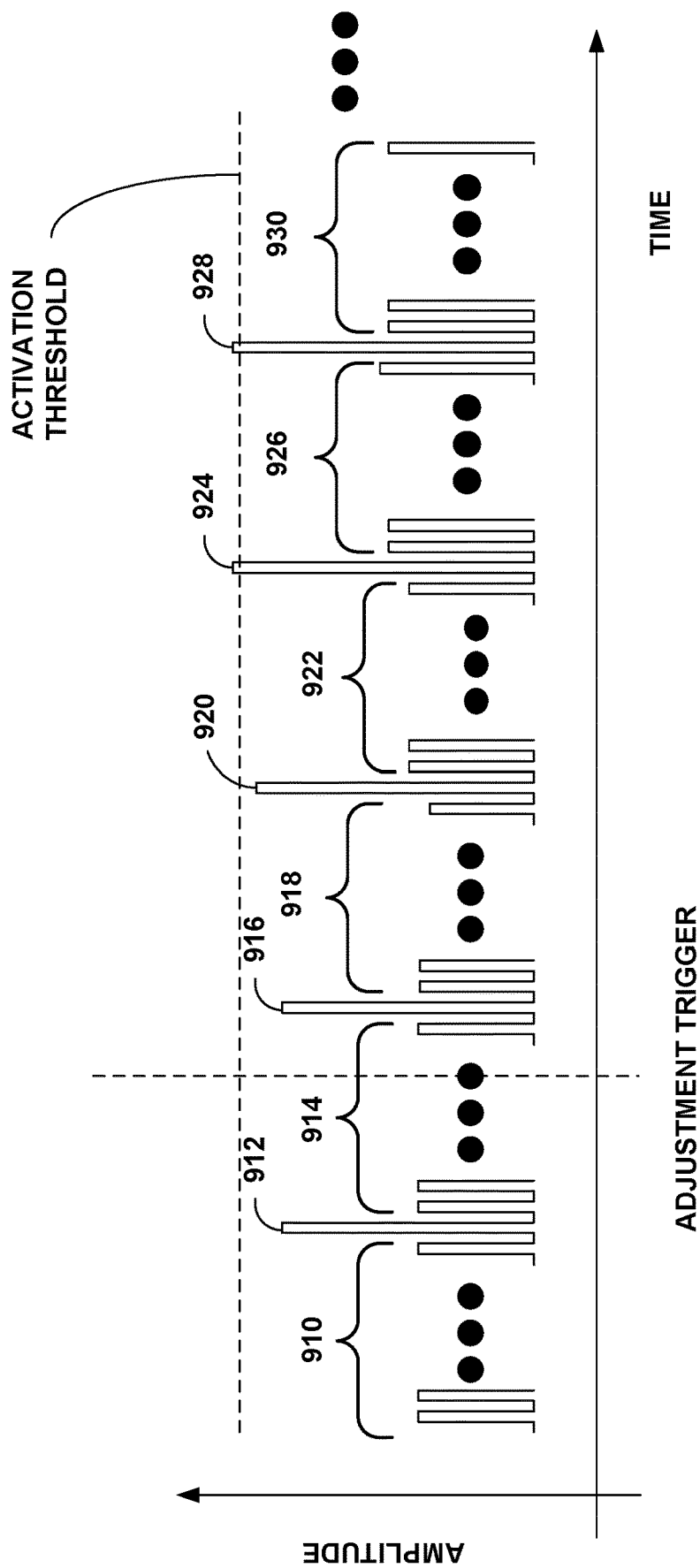
FIG. 9 is another timing diagram illustrating an example operation for delivering therapy according to the techniques of this disclosure.

FIG. 8 is a timing diagram illustrating an example operation for delivering therapy according to the techniques of this disclosure. FIG. 9 is another timing diagram illustrating an example operation for delivering therapy according to the techniques of this disclosure. For brevity, FIGS. 8 and 9 are described together.

In FIGS. 8 and 9, IMD 102 may be delivering a first set of pulses having a first amplitude and a second set of pulses having a second larger amplitude, where one or more pulses having the second amplitude are intermingled with groups of pulses having the first amplitude. As illustrated in FIG. 8, pulse 812 is delivered between sequential group of pulses 810 and group of pulses 814, and the amplitude of pulse 812 is greater than that of group of pulses 810, 814. In FIG. 9, pulse 912 is delivered between sequential group of pulses 910 and group of pulses 914, and the amplitude of pulse 912 is greater than that of pulses 910 and 914. In FIG. 8, delivery of pulse 812 may cause an action potential to be evoked because the amplitude of pulse 812 is greater than the activation threshold. However, in FIG. 9, delivery of pulse 912 may not cause an action potential to be evoked because the amplitude of pulse 912 is less than the activation threshold.

In FIGS. 8 and 9, the duration of each of groups of pulses 810, 814, 910, and 914 are all approximately the same period of time (e.g., each is the amount of time to deliver approximately 200 pulses). A pulse having a larger amplitude is then delivered after each of these groups. Therefore, each of the pulses having the larger amplitude are delivered less frequently than those having the smaller amplitude (e.g., there are more pulses in the groups of pulses 810, 814, 910, and 914, than the number of pulses having the larger amplitude that are intermingled with these groups). In FIG. 8, because delivery of a pulse having an amplitude greater than the activation threshold is relatively infrequent (e.g., every 50 Hz), the patient may not experience discomfort.

At a time after delivery of pulse 812 and 912, an adjustment trigger may occur. An adjustment trigger may be any event that causes IMD 102 adjust the therapy parameters. The adjustment trigger may be set to occur periodically, randomly, or in response to an event (e.g., change in posture, motion, lead/electrode impedance, lead/electrode position, and the like). There may other reasons for adjusting therapy and the techniques are not limited to the above examples.

After the adjustment trigger, processor 210 may determine whether an action potential was evoked after delivery of a pulse having the larger amplitude. For example, in FIG. 8, after delivery of pulse 816, processor 210 may determine that an action potential was evoked, and in FIG. 9, after delivery of pulse 916, processor 210 may determine that an action potential was not evoked. In the example of FIG. 8, processor 210 may determine that the first amplitude is too high because an action potential was evoked by delivery of the pulse having the second amplitude. In the example of FIG. 9, processor 210 may determine that the first amplitude is too low because an action potential was not evoked by delivery of the pulse having the second amplitude.

Processor 210 may adjust downward the second amplitude in FIG. 8, and adjust upward the second amplitude in FIG. 9. For instance, in FIG. 8, after delivery of another group of pulses 818 having the first amplitude, processor 210 may cause stimulation generator 202 to output a pulse 820 have a lower amplitude than pulse 816. In FIG. 9, after delivery of another group of pulses 918 having the first amplitude, processor 210 may cause stimulation generator 202 to output a pulse 920 have a higher amplitude than pulse 916.

In FIG. 8, after delivery of pulse 820, an action potential may still be evoked (e.g., the amplitude of pulse 820 is greater than the activation threshold). In FIG. 9, after delivery of pulse 920, an action potential may still not be evoked (e.g., the amplitude of pulse 920 is less than the activation threshold). In FIG. 8, because the adjusted second amplitude is still greater than or equal to the activation threshold, processor 210 may keep adjusting the amplitude downwards. In FIG. 9, because the adjusted second amplitude is still not greater than or equal to the activation threshold, processor 210 may keep adjusting the amplitude upwards.

In FIG. 8, processor 210 may keep adjusting the amplitude downwards until stimulation generator 202 delivers pulse 824, and pulse 824 may not evoke an action potential because the amplitude of pulse 824 is less than the activation threshold. In FIG. 9, processor 210 may keep adjusting the amplitude upwards until stimulation generator 202 delivers pulse 924, and pulse 924 may evoke an action potential because the amplitude of pulse 924 is greater than the activation threshold.

In addition, processor 210 may also adjust the first amplitude based on the adjusted second amplitude. For example, group of pulses 818 have a lower amplitude than group of pulses 814, group of pulses 822 have a lower amplitude than group of pulses 818, and group of pulses 826 have a lower amplitude than group of pulses 822. In this example, processor 210 set the amplitude of group of pulses 814 based on the amplitude of pulse 812, set the amplitude of group of pulses 818 based on the amplitude of pulse 816, set the amplitude of group of pulses 822 based on the amplitude of pulse 820, and set the amplitude of group of pulses 826 based on the amplitude of pulse 824. Because the amplitude of pulse 816 is less than pulse 812, the amplitude of group of pulses 818 is less than group of pulses 814, because the amplitude of pulse 820 is less than pulse 816, the amplitude of group of pulses 822 is less than group of pulses 818, and because the amplitude of pulse 824 is less than pulse 820, the amplitude of group of pulses 826 is less than group of pulses 822.

Similarly, for FIG. 9, group of pulses 818 have a lower amplitude than group of pulses 922, and group of pulses 922 have a lower amplitude than group of pulses 926. In this example, processor 210 set the amplitude of group of pulses 918 based on the amplitude of pulse 916, set the amplitude of group of pulses 922 based on the amplitude of pulse 920, and set the amplitude of group of pulses 926 based on the amplitude of pulse 924. Because the amplitude of pulse 920 is greater than pulse 916, the amplitude of group of pulses 922 is greater than group of pulses 918, and because the amplitude of pulse 924 is greater than pulse 920, the amplitude of group of pulses 926 is greater than group of pulses 922.

In this way, processor 210 may adjust amplitudes upwards or downwards to adjust the therapy using a pulse having a larger amplitude relative to sequential groups of pulses as a way to titrate the amplitude. For example, if the amplitude is too low to evoke the action potential, processor 210 may increase the amplitude until greater than or equal to an activation threshold, and if the amplitude is too high that the action potential is evoked, processor 210 may decrease the amplitude until less than or equal to the activation threshold.

However, in one example, processor 210 may delay the sending of the higher frequency pulses until the lower frequency pulses have been properly adjusted, then the higher frequency pulses would begin again at the threshold determined by the relation to the amplitude of the lower frequency pulses. For example, processor 210 may first determine the amplitude of the lower frequency pulses, and during this determination may not cause IMD 102 to deliver any higher frequency pulses. Then, after determining the amplitude of the lower frequency pulses, processor 210 may determine the amplitude of the higher frequency pulses and cause IMD 102 to deliver the higher frequency pulses.

Accordingly, FIGS. 8 and 9 illustrate examples where processor 210 adjusts amplitudes of pulses delivered at the lower frequency until the amplitude of these pulses is greater than or equal to an activation threshold based on the lower frequency pulses being less than the activation threshold prior to adjustment or until the amplitude of these pulses is less than or equal to the activation threshold based on the lower frequency pulses being greater than the activation threshold prior to adjustment. In some examples, to adjust the amplitudes of the low frequency pulses, processor 210 may adjust the amplitude of the low frequency pulses by an adjustment amount (e.g., amplitude of pulse 816 to amplitude of pulse 820 or amplitude of pulse 916 to amplitude of pulse 920). Processor 210 may determine whether an action potential is evoked when low frequency stimulation pulses having the adjusted amplitude are delivered. Processor 210 may further adjust the adjusted amplitude for the low frequency stimulation pulses until delivery of the low frequency stimulation pulses having the adjusted amplitude cause the action potential to be evoked (e.g., such as in FIG. 9) or until delivery of the low frequency stimulation pulses having the adjusted amplitude do not cause the action potential to be evoked (e.g., such as in FIG. 8). In FIGS. 8 and 9, the amplitude of the higher frequency pulses may be adjusted during the adjustment of the lower frequency pulses. In some examples, the amplitude of the higher frequency pulses may not be adjusted until after the completion of the adjustment of the amplitude of the lower frequency pulses.

Figure 10:
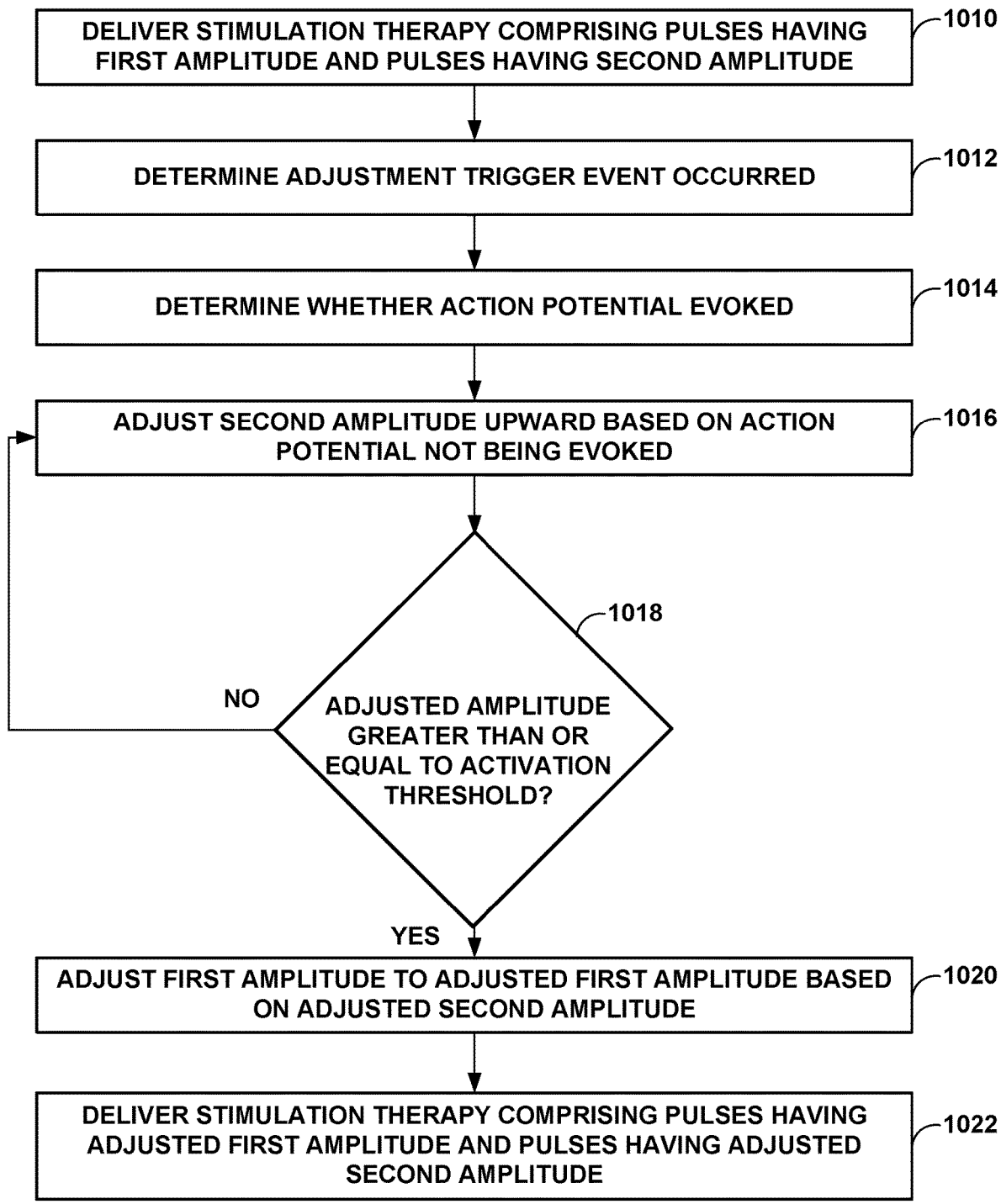
FIG. 10 is a flowchart illustrating an example operation for delivering therapy according to the techniques of this disclosure.

FIG. 10 is a flowchart illustrating an example operation for delivering therapy according to the techniques of this disclosure. FIG. 10 is described with processor 210 performing example operations, but such operations may be performed with processor 310, or a combination of processor 210 and processor 310. Accordingly, the example techniques described in this disclosure, generally, and in FIG. 10 may be performed by processing circuitry comprising at least one of fixed-function or programmable circuitry, where examples of the processing circuitry include processor 210, processor 310, or a combination thereof.

Stimulation generator 202 may deliver stimulation therapy comprising a first set of plurality of pulses having a first amplitude, and a second set of plurality of pulses having a second amplitude, where one or more pulses having the second amplitude are intermingled with sequential groups of pulses having the first amplitude (1010). For example, stimulation generator may repeat alternate delivery of the groups of pulses of the first set of plurality of pulses for respective periods (e.g., the amount of time for 200 pulses) and the one or more pulses of the second set of plurality of pulses at least until an adjustment to the second amplitude is to be made.

Processor 210 may determine whether an adjustment trigger event occurred (1012). For example, processor 210 may determine whether there was change in posture or motion based on an output from an accelerometer, change in lead impedance, change in lead position, and the like.

Processor 210 may determine whether an action potential evoked (1014). For example, after the adjustment trigger occurred, processor 210 may determine whether an action potential is evoked based on the delivery of a pulse having the second amplitude. There may be various ways in which processor 210 may determine whether an action potential evoked such as the various sensing example operations described above.

Based on action potential not being evoked, processor 210 may adjust the second amplitude upwards (1016). Processor 210 may then determine if the adjusted second amplitude is greater than or equal to activation threshold (1018). For example, processor 210 may determine if an action potential is evoked or not evoked. If evoked, then the adjusted amplitude is greater than or equal to the activation threshold, and if not evoked, then the adjusted amplitude is not greater than or equal to the activation threshold.

If the adjusted amplitude is not greater than or equal to the activation threshold (NO of 1018), processor 210 may keep adjusting the second amplitude until the adjusted second amplitude is greater than or equal to the activation threshold. If the adjusted amplitude is greater than or equal to the activation threshold (YES of 1018), processor 210 may adjust the first amplitude to an adjusted first amplitude based on the adjusted second amplitude (1020) (e.g., multiply the second adjusted amplitude with a certain ratio to determine the first adjusted amplitude).

In the example illustrated in FIG. 10, processor 210 is described as adjusting the first amplitude to the adjusted first amplitude after the adjusted second amplitude is greater than or equal to the activation threshold. However, the example techniques are not so limited. In some examples, processor 210 may adjust the first amplitude during the adjusting of the second amplitude. For example, after a first adjustment of the second amplitude, the adjusted second amplitude may be less than the activation threshold. In this example, processor 210 may also increase the first amplitude. Then, after a second adjustment of adjusted second amplitude, the adjusted second amplitude may be greater than or equal to the activation threshold, and processor 210 may further adjust the adjusted first amplitude. Accordingly, in some examples, processor 210 may adjust the second and first amplitudes together until the adjusted second amplitude is greater than or equal to the activation threshold, and in some examples, processor 210 may adjust the second amplitude until the adjusted second amplitude is greater than or equal to the activation threshold, and then adjust the first amplitude to the adjusted first amplitude.

In some examples, to adjust the second amplitude, processor 210 may be configured to adjust the second amplitude by an adjustment amount (e.g., as illustrated in FIG. 9) to the adjusted second amplitude. Processor 210 may determine whether an action potential is evoked when stimulation pulses having the adjusted second amplitude are delivered, and further adjust the adjusted second amplitude until delivery of stimulation pulses having the adjusted second amplitude causes the action potential to be evoked. Processor 210 may adjust the first amplitude during the further adjusting of the adjusted second amplitude, or adjust the first amplitude after completion of the adjusting the second amplitude. In this disclosure, the adjusted second amplitude is used to refer to the second amplitude being adjusted to reach the final adjusted second amplitude or during the adjustment of the second amplitude while the adjusted second amplitude reaches the final adjusted second amplitude.

Processor 210 may then cause stimulation generator 202 to deliver stimulation therapy based at least on the adjusted first amplitude. For example, processor 210 may then cause stimulation generator 202 to deliver stimulation therapy comprising a third set of pulses having the adjusted first amplitude, and a fourth set of pulses having the adjusted second amplitude (1022). In this example, one or more pulses of the second adjusted amplitude are intermingled with sequential groups of pulses having the first adjusted amplitude.

Figure 11:
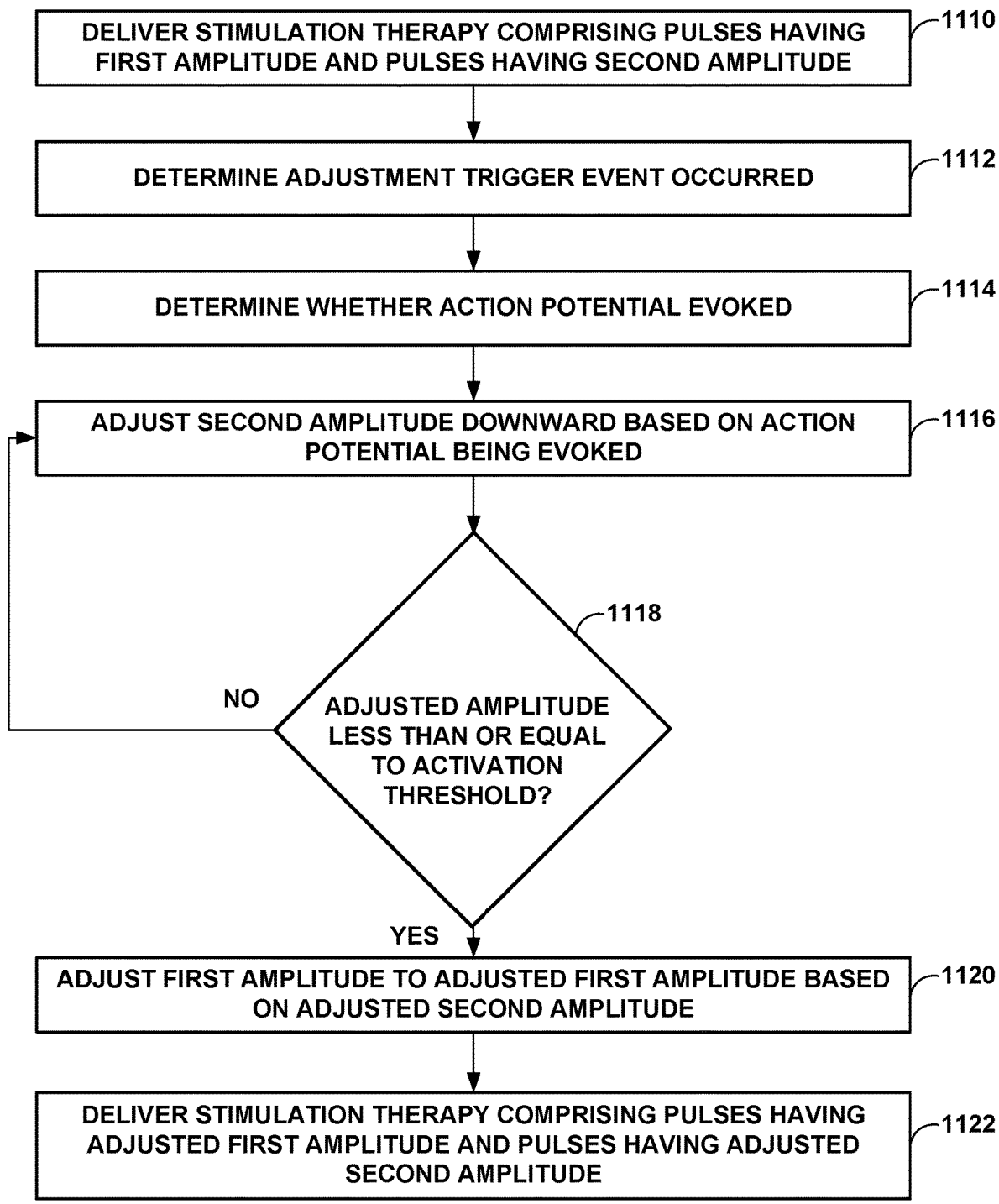
FIG. 11 is a flowchart illustrating an example operation for delivering therapy according to the techniques of this disclosure.

FIG. 11 is a flowchart illustrating an example operation for delivering therapy according to the techniques of this disclosure. FIG. 101 is described with processor 210 performing example operations, but such operations may be performed with processor 310, or a combination of processor 210 and processor 310. Accordingly, the example techniques described in this disclosure, generally, and in FIG. 11 may be performed by processing circuitry comprising at least one of fixed-function or programmable circuitry, where examples of the processing circuitry include processor 210, processor 310, or a combination thereof.

Stimulation generator 202 may deliver stimulation therapy comprising a first set of plurality of pulses having a first amplitude, and a second set of plurality of pulses having a second amplitude, where one or more pulses having the second amplitude are intermingled with sequential groups of pulses having the first amplitude (1110). For example, stimulation generator may repeat alternate delivery of the groups of pulses of the first set of plurality of pulses for respective periods (e.g., the amount of time for 200 pulses) and the one or more pulses of the second set of plurality of pulses at least until an adjustment to the second amplitude is to be made.

Processor 210 may determine whether an adjustment trigger event occurred (1112). For example, processor 210 may determine whether there was change in posture or motion based on an output from an accelerometer, change in lead impedance, change in lead position, and the like.

Processor 210 may determine whether an action potential evoked (1114). For example, after the adjustment trigger occurred, processor 210 may determine whether an action potential is evoked based on the delivery of a pulse having the second amplitude. There may be various ways in which processor 210 may determine whether an action potential evoked such as the various sensing example operations described above.

Based on action potential being evoked, processor 210 may adjust the second amplitude downwards (1116). Processor 210 may then determine if the adjusted second amplitude is less than or equal to activation threshold (1118). For example, processor 210 may determine if an action potential is evoked or not evoked. If evoked, then the adjusted amplitude is not less than or equal to the activation threshold, and if not evoked, then the adjusted amplitude is less than or equal to the activation threshold.

If the adjusted amplitude is not less than or equal to the activation threshold (NO of 1118), processor 210 may keep adjusting the second amplitude until the adjusted second amplitude is less than or equal to the activation threshold. If the adjusted amplitude is less than or equal to the activation threshold (YES of 1118), processor 210 may adjust the first amplitude to an adjusted first amplitude based on the adjusted second amplitude (1120) (e.g., multiply the second adjusted amplitude with a certain ratio to determine the first adjusted amplitude).

In the example illustrated in FIG. 11, processor 210 is described as adjusting the first amplitude to the adjusted first amplitude after the adjusted second amplitude is less than or equal to the activation threshold. However, the example techniques are not so limited. In some examples, processor 210 may adjust the first amplitude during the adjusting of the second amplitude. For example, after a first adjustment of the second amplitude, the adjusted second amplitude may be greater than the activation threshold. In this example, processor 210 may also decrease the first amplitude. Then, after a second adjustment of adjusted second amplitude, the adjusted second amplitude may be less than or equal to the activation threshold, and processor 210 may further adjust the adjusted first amplitude. Accordingly, in some examples, processor 210 may adjust the second and first amplitudes together until the adjusted second amplitude is less than or equal to the activation threshold, and in some examples, processor 210 may adjust the second amplitude until the adjusted second amplitude is less than or equal to the activation threshold, and then adjust the first amplitude to the adjusted first amplitude.

In some examples, to adjust the second amplitude, processor 210 may be configured to adjust the second amplitude by an adjustment amount (e.g., as illustrated in FIG. 8) to the adjusted second amplitude. Processor 210 may determine whether an action potential is evoked when stimulation pulses having the adjusted second amplitude are delivered, and further adjust the adjusted second amplitude until delivery of stimulation pulses having the adjusted second amplitude does not cause the action potential to be evoked. Processor 210 may adjust the first amplitude during the further adjusting of the adjusted second amplitude, or adjust the first amplitude after completion of the adjusting the second amplitude. In this disclosure, the adjusted second amplitude is used to refer to the second amplitude being adjusted to reach the final adjusted second amplitude or during the adjustment of the second amplitude while the adjusted second amplitude reaches the final adjusted second amplitude.

Processor 210 may then cause stimulation generator 202 to deliver stimulation therapy based at least on the adjusted first amplitude. For example, processor 210 may then cause stimulation generator 202 to deliver stimulation therapy comprising a third set of pulses having the adjusted first amplitude, and a fourth set of pulses having the adjusted second amplitude (1122). In this example, one or more pulses of the second adjusted amplitude are intermingled with sequential groups of pulses having the first adjusted amplitude.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
delivering stimulation therapy comprising a first set of a plurality of pulses having a first amplitude, and a second set of a plurality of pulses having a second amplitude greater than the first amplitude, wherein one or more pulses of the second set of plurality of pulses are intermingled with sequential groups of pulses of the first set of plurality of pulses;
adjusting the second amplitude to an adjusted second amplitude until the adjusted second amplitude is one of:
greater than or equal to an activation threshold based on the second amplitude being less than the activation threshold, or
less than or equal to the activation threshold based on the second amplitude being greater than the activation threshold;
adjusting the first amplitude to an adjusted first amplitude based on the adjusted second amplitude; and
delivering stimulation therapy based at least on the adjusted first amplitude.

2. The method of claim 1,
wherein delivery of pulses at the activation threshold evokes an action potential,
wherein adjusting the second amplitude to the adjusted second amplitude until the adjusted second amplitude is greater than or equal to the activation threshold comprises:
determining whether the action potential is invoked; and
adjusting the second amplitude upwards until determined that the action potential is evoked, and
wherein adjusting the second amplitude to the adjusted second amplitude until the adjusted second amplitude is less than or equal to the activation threshold comprises:
determining whether the action potential is invoked; and
adjusting the second amplitude downwards until determined that the action potential is not evoked.

3. The method of claim 2, further comprising:
after adjusting the second amplitude upwards until determined that the action potential is evoked, reducing the adjusted second amplitude until the adjusted second amplitude is substantially equal to the activation threshold.

4. The method of claim 2, further comprising:
after adjusting the second amplitude downwards until determined that the action potential is not evoked, increasing the adjusted second amplitude until the adjusted second amplitude is substantially equal to the activation threshold.

5. The method of claim 1, further comprising:
determining motion or posture based on an output from an accelerometer,
wherein adjusting the second amplitude comprises adjusting the second amplitude to the adjusted second amplitude based on the determined motion or posture.

6. The method of claim 1, wherein delivering stimulation therapy comprising the first set of plurality of pulses having the first amplitude, and the second set of plurality of pulses having the second amplitude comprises:
repeating alternate delivery of the groups of pulses of the first set of plurality of pulses for respective periods of time and the one or more pulses of the second set of plurality of pulses at least until the adjustment of the second amplitude.

7. The method of claim 6, wherein the respective periods of time for each group of pulses of the first set of plurality of pulses is the same.

8. The method of claim 1, wherein one or more pulses of groups of pulses of the first set of plurality of pulses comprise a first pulse width, and wherein the one or more pulses of the second set of plurality of pulses comprises a second, different pulse width.

9. The method of claim 1, wherein delivering stimulation therapy based at least on the adjusted first amplitude comprises delivering stimulation therapy comprising a third set of a plurality of pulses having the adjusted first amplitude, and a fourth set of plurality of pulses having the adjusted second amplitude, wherein one or more pulses of the fourth set of plurality of pulses are intermingled with sequential groups of pulses of the third set of plurality of pulses.

10. The method of claim 9, wherein one or more pulses of groups of pulses of the third set of plurality of pulses comprise the first pulse width, and wherein the one or more pulses of the fourth set of plurality of pulses comprises the second pulse width.

11. The method of claim 9, wherein delivering stimulation therapy comprising the third set of plurality of pulses having the adjusted first amplitude, and the fourth set of plurality of pulses having the adjusted second amplitude comprises:
delivering the third set of plurality of pulses with a first set of electrodes on a lead to deliver relatively high frequency stimulation therapy; and
delivering the fourth set of plurality of pulses with a second set of electrodes on the lead to deliver relatively low frequency stimulation therapy.

12. The method of claim 9, wherein the groups of pulses of the first set of plurality of pulses include more pulses than the one or more pulses of the second set of plurality of pulses intermingled with the sequential groups of pulses of the first set of plurality of pulses, and wherein each group of pulses of the third set of plurality of pulses includes more pulses than the one or more pulses of the fourth set of plurality of pulses intermingled with the sequential groups of pulses of the third set of plurality of pulses.

13. The method of claim 1, wherein adjusting the second amplitude comprises adjusting the second amplitude at set time intervals.

14. The method of claim 1, wherein adjusting the first amplitude to the adjusted first amplitude comprises adjusting the first amplitude during the adjusting of the second amplitude to the adjusted second amplitude.

15. The method of claim 1, wherein adjusting the second amplitude comprises:
adjusting the second amplitude by an adjustment amount to the adjusted second amplitude;
determining whether an action potential is evoked when stimulation pulses having the adjusted second amplitude are delivered; and
further adjusting the adjusted second amplitude until:
delivery of stimulation pulses having the adjusted second amplitude causes the action potential to be evoked based on the second amplitude being less than the activation threshold, or delivery of stimulation pulses having the adjusted second amplitude does not cause the action potential to be evoked based on the second amplitude being greater than the activation threshold.

16. The method of claim 15, wherein adjusting the first amplitude comprises adjusting the first amplitude during the further adjusting of the adjusted second amplitude.

17. The method of claim 1, wherein delivering stimulation therapy comprising the first set of plurality of pulses having the first amplitude, and the second set of the plurality of pulses having the second amplitude comprises:

delivering a pulse having the second amplitude;
delaying delivery of pulses having the first amplitude until after determination is made as to whether an action potential is evoked; and
delivering pulses having the first amplitude after the delay.

18. A medical system comprising:
at least one stimulation generator; and
a processing circuitry comprising at least one of fixed-function or programmable circuitry, the processing circuitry configured to:
cause the at least one stimulation generator to deliver stimulation therapy comprising a first set of a plurality of pulses having a first amplitude, and a second set of a plurality of pulses having a second amplitude greater than the first amplitude, wherein one or more pulses of the second set of plurality of pulses are intermingled with sequential groups of pulses of the first set of plurality of pulses;
adjust the second amplitude to an adjusted second amplitude until the adjusted second amplitude is one of:
greater than or equal to an activation threshold based on the second amplitude being less than the activation threshold, or
less than or equal to the activation threshold based on the second amplitude being greater than the activation threshold;
adjust the first amplitude to an adjusted first amplitude based on the adjusted second amplitude; and
cause the at least one stimulation generator to deliver stimulation therapy based at least on the adjusted first amplitude.

19. The system of claim 18, further comprising an implantable medical device (IMD), wherein the IMD comprises the processing circuitry and the stimulation generator.

20. The system of claim 18, further comprising an implantable medical device (IMD) and an external programmer, wherein the IMD comprises the stimulation generator, and the external programmer comprises the processing circuitry.

21. The system of claim 18,
wherein delivery of pulses at the activation threshold evokes an action potential,
wherein to adjust the second amplitude to the adjusted second amplitude until the adjusted second amplitude is greater than or equal to the activation threshold, the processing circuitry is configured to:
determine whether the action potential is invoked; and
adjust the second amplitude upwards until determined that the action potential is evoked, and
wherein to adjust the second amplitude to the adjusted second amplitude until the adjusted second amplitude is less than or equal to the activation threshold, the processing circuitry is configured to:
determine whether the action potential is invoked; and
adjust the second amplitude downwards until determined that the action potential is not evoked.

22. The system of claim 21, wherein after adjusting the second amplitude upwards until determined that the action potential is evoked, the processing circuitry is configured to reduce the adjusted second amplitude until the adjusted second amplitude is substantially equal to the activation threshold.

23. The system of claim 21, wherein after adjusting the second amplitude downwards until determined that the action potential is not evoked, the processing circuitry is configured to increase the adjusted second amplitude until the adjusted second amplitude is substantially equal to the activation threshold.

24. The system of claim 18, wherein the processing circuitry is configured to determine motion or posture based on an output from an accelerometer, and wherein to adjust the second amplitude, the processing circuitry is configured to adjust the second amplitude to the adjusted second amplitude based on the determined motion or posture.

25. The system of claim 18, wherein to cause the stimulation generator to deliver stimulation therapy comprising the first set of plurality of pulses having the first amplitude, and the second set of plurality of pulses having the second amplitude, the processing circuitry is configured to cause the stimulation generator to:
repeat alternate delivery of the groups of pulses of the first set of plurality of pulses for respective periods of time and the one or more pulses of the second set of plurality of pulses at least until the adjustment of the second amplitude.

26. The system of claim 25, wherein the respective periods of time for each group of pulses of the first set of plurality of pulses is the same.

27. The system of claim 18, wherein one or more pulses of groups of pulses of the first set of plurality of pulses comprise a first pulse width, and wherein the one or more pulses of the second set of plurality of pulses comprises a second, different pulse width.

28. The system of claim 18, wherein to cause the stimulation generator to deliver stimulation therapy based at least on the adjusted first amplitude, the processing circuitry is configured to cause the stimulation generator to deliver stimulation therapy comprising a third set of a plurality of pulses having the adjusted first amplitude, and a fourth set of plurality of pulses having the adjusted second amplitude, wherein one or more pulses of the fourth set of plurality of pulses are intermingled with sequential groups of pulses of the third set of plurality of pulses.

29. The system of claim 28, wherein one or more pulses of groups of pulses of the third set of plurality of pulses comprise the first pulse width, and wherein the one or more pulses of the fourth set of plurality of pulses comprises the second pulse width.

30. The system of claim 28, wherein to cause the stimulation generator to deliver stimulation therapy comprising the third set of plurality of pulses having the adjusted first amplitude, and the fourth set of plurality of pulses having the adjusted second amplitude, the processing circuitry is configured to cause the stimulation generator to:
deliver the third set of plurality of pulses with a first set of electrodes on a lead to deliver relatively high frequency stimulation therapy; and deliver the fourth set of plurality of pulses with a second set of electrodes on the lead to deliver relatively low frequency stimulation therapy.

31. The system of any of claims 28, wherein the groups of pulses of the first set of plurality of pulses include more pulses than the one or more pulses of the second set of plurality of pulses intermingled with the sequential groups of pulses of the first set of plurality of pulses, and wherein each group of pulses of the third set of plurality of pulses includes more pulses than the one or more pulses of the fourth set of plurality of pulses intermingled with the sequential groups of pulses of the third set of plurality of pulses.

32. The system of claim 18, wherein to adjust the second amplitude, the processing circuitry is configured to adjust the second amplitude at set time intervals.

33. The system of claim 18, wherein to adjust the first amplitude to the adjusted first amplitude, the processing circuitry is configured to adjust the first amplitude during the adjusting of the second amplitude to the adjusted second amplitude.

34. The system of claim 18, wherein to adjust the second amplitude, the processing circuitry is configured to:
  adjust the second amplitude by an adjustment amount to the adjusted second amplitude;
  determine whether an action potential is evoked when stimulation pulses having the adjusted second amplitude are delivered; and
  further adjust the adjusted second amplitude until:
    delivery of stimulation pulses having the adjusted second amplitude causes the action potential to be evoked based on the second amplitude being less than the activation threshold, or
    delivery of stimulation pulses having the adjusted second amplitude does not cause the action potential to be evoked based on the second amplitude being greater than the activation threshold.

35. The system of claim 34, wherein to adjust the first amplitude, the processing circuitry is configured to adjust the first amplitude during the further adjusting of the adjusted second amplitude.

36. The system of claim 18, wherein to cause the stimulation generator to deliver stimulation therapy comprising the first set of plurality of pulses having the first amplitude, and the second set of the plurality of pulses having the second amplitude, the processing circuitry is configured to cause the stimulation generator to:
  deliver a pulse having the second amplitude;
  delay delivery of pulses having the first amplitude until after determination is made as to whether an action potential is evoked; and
  deliver pulses having the first amplitude after the delay.

37. A computer-readable storage medium storing instructions that when executed cause one or more processors to:
  cause at least one stimulation generator to deliver stimulation therapy comprising a first set of a plurality of pulses having a first amplitude, and a second set of a plurality of pulses having a second amplitude greater than the first amplitude, wherein one or more pulses of the second set of plurality of pulses are intermingled with sequential groups of pulses of the first set of plurality of pulses;
  adjust the second amplitude to an adjusted second amplitude until the adjusted second amplitude is one of:
    greater than or equal to an activation threshold based on the second amplitude being less than the activation threshold, or
    less than or equal to the activation threshold based on the second amplitude being greater than the activation threshold;
  adjust the first amplitude to an adjusted first amplitude based on the adjusted second amplitude; and
  cause the at least one stimulation generator to deliver stimulation therapy based at least on the adjusted first amplitude.

* * * * *